United States Patent
Adams et al.

(10) Patent No.: US 10,682,460 B2
(45) Date of Patent: Jun. 16, 2020

(54) MEDICATION SAFETY DEVICES AND METHODS

(71) Applicant: Smiths Medical ASD, Inc., Rockland, MA (US)

(72) Inventors: Grant Adams, Coon Rapids, MN (US); Eric Wilkowske, North Oaks, MN (US); Alison Bloomquist, Gem Lake, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 469 days.

(21) Appl. No.: 14/763,985

(22) PCT Filed: Jan. 23, 2014

(86) PCT No.: PCT/US2014/012757
§ 371 (c)(1),
(2) Date: Jul. 28, 2015

(87) PCT Pub. No.: WO2014/116832
PCT Pub. Date: Jul. 31, 2014

(65) Prior Publication Data
US 2015/0367065 A1 Dec. 24, 2015

Related U.S. Application Data

(60) Provisional application No. 61/757,587, filed on Jan. 28, 2013, provisional application No. 61/826,253, filed on May 22, 2013.

(51) Int. Cl.
*A61M 5/142* (2006.01)
*G06F 19/00* (2018.01)
(Continued)

(52) U.S. Cl.
CPC ........ *A61M 5/14216* (2013.01); *A61M 5/142* (2013.01); *G06F 3/04847* (2013.01);
(Continued)

(58) Field of Classification Search
CPC .............. G06F 19/326; G06F 19/3468; A61M 2005/14208; G16H 20/10
See application file for complete search history.

(56) References Cited

U.S. PATENT DOCUMENTS

| | | |
|---|---|---|
| 2,968,804 A | 1/1961 | Buffington |
| 3,555,286 A | 1/1971 | Cote |

(Continued)

FOREIGN PATENT DOCUMENTS

| | | |
|---|---|---|
| CA | 2060151 | 8/1992 |
| CA | 2511931 | 7/2004 |

(Continued)

OTHER PUBLICATIONS

International Search Report, Application No. PCT/US2014/012757, dated May 29, 2014, 4 pages.

(Continued)

*Primary Examiner* — Sheetal R Paulson
(74) *Attorney, Agent, or Firm* — Patterson Thuente Pedersen, P.A.

(57) ABSTRACT

A medication safety device and method can include an infusion pump and a drug library in communication with the infusion pump. The drug library can have upper hard and soft limits and lower hard and soft limits associated with at least one drug. A graphical user interface can display a bar chart showing upper and lower soft limit bars for the at least one drug. The upper and lower soft limit bars can be grabbed and dragged on the graphical user interface in touch screen fashion to new positions associated with new upper and lower soft limits. The graphical user interface and associated (Continued)

hardware and software can be configurable to responsively re analyze data and compare a particular infusion to the new upper and lower soft limits.

22 Claims, 9 Drawing Sheets

(51) Int. Cl.
    *G16H 40/63*     (2018.01)
    *G16H 50/70*     (2018.01)
    *G06F 16/248*     (2019.01)
    *G06F 3/0484*     (2013.01)
    *G06F 16/2457*     (2019.01)

(52) U.S. Cl.
    CPC ...... *G06F 16/248* (2019.01); *G06F 16/24578* (2019.01); *G06F 19/326* (2013.01); *G06F 19/3468* (2013.01); *G16H 40/63* (2018.01); *G16H 50/70* (2018.01); *A61M 2005/14208* (2013.01); *A61M 2205/3576* (2013.01); *A61M 2205/502* (2013.01); *A61M 2205/505* (2013.01); *A61M 2205/52* (2013.01)

(56) References Cited

U.S. PATENT DOCUMENTS

| | | |
|---|---|---|
| 3,603,152 A | 9/1971 | Alibert et al. |
| 3,777,165 A | 12/1973 | Bryant et al. |
| 3,809,871 A | 5/1974 | Howard et al. |
| 3,923,060 A | 12/1975 | Ellinwood, Jr. |
| 3,942,526 A | 3/1976 | Wilder et al. |
| 3,985,133 A | 10/1976 | Jenkins et al. |
| 4,027,536 A | 6/1977 | Heggie |
| T961,004 I4 | 8/1977 | Horton |
| 4,080,967 A | 3/1978 | O'Leary |
| 4,091,550 A | 5/1978 | Schrenk et al. |
| 4,098,267 A | 7/1978 | Stein et al. |
| 4,137,913 A | 2/1979 | Georgi |
| 4,141,252 A | 2/1979 | Lodge |
| 4,146,029 A | 3/1979 | Ellinwood, Jr. |
| 4,174,637 A | 11/1979 | Mulzet et al. |
| 4,184,815 A | 1/1980 | Casson et al. |
| 4,191,184 A | 3/1980 | Carlisle |
| 4,210,138 A | 7/1980 | Jess et al. |
| 4,213,454 A | 7/1980 | Shim |
| 4,217,993 A | 8/1980 | Jess et al. |
| 4,236,880 A | 12/1980 | Archibald |
| 4,270,532 A | 6/1981 | Frametzki et al. |
| 4,279,188 A | 7/1981 | Scott |
| 4,280,136 A | 7/1981 | Kasbima et al. |
| 4,282,872 A | 8/1981 | Franetzki et al. |
| 4,299,218 A | 11/1981 | Knigge et al. |
| 4,299,541 A | 11/1981 | Ohara et al. |
| 4,308,866 A | 1/1982 | Jelliffe et al. |
| 4,309,993 A | 1/1982 | Brown |
| 4,311,377 A | 1/1982 | Matteson |
| 4,314,227 A | 2/1982 | Eventoff |
| 4,314,228 A | 2/1982 | Eventoff |
| 4,315,238 A | 2/1982 | Eventoff |
| 4,320,757 A | 3/1982 | Whitney et al. |
| 4,368,645 A | 1/1983 | Glenn et al. |
| 4,369,780 A | 1/1983 | Sakai |
| 4,370,983 A | 2/1983 | Lichtenstein |
| 4,373,525 A | 2/1983 | Kobayashi |
| 4,373,527 A | 2/1983 | Fischell |
| 4,385,630 A | 5/1983 | Gilcher et al. |
| 4,385,958 A | 5/1983 | Long |
| RE31,315 E | 7/1983 | Jenkins et al. |
| 4,392,849 A | 7/1983 | Petre et al. |
| 4,394,862 A | 7/1983 | Shim |
| 4,395,259 A | 7/1983 | Prestele et al. |
| 4,396,977 A | 8/1983 | Slater et al. |
| 4,398,542 A | 8/1983 | Cunningham et al. |
| 4,410,322 A | 10/1983 | Archibald |
| 4,413,314 A | 11/1983 | Slater et al. |
| 4,425,661 A | 1/1984 | Moses et al. |
| 4,431,425 A | 2/1984 | Thompson et al. |
| 4,443,218 A | 4/1984 | DeCant, Jr. et al. |
| 4,446,344 A | 5/1984 | Fiedler |
| 4,460,355 A | 7/1984 | Layman |
| 4,484,479 A | 11/1984 | Eckhardt |
| 4,489,302 A | 12/1984 | Eventoff |
| 4,490,798 A | 12/1984 | Franks et al. |
| 4,493,704 A | 1/1985 | Beard et al. |
| 4,494,950 A | 1/1985 | Fischell |
| 4,498,843 A | 2/1985 | Schneider et al. |
| 4,512,013 A | 4/1985 | Nash et al. |
| 4,520,706 A | 6/1985 | Deforeit |
| 4,526,574 A | 7/1985 | Pekkarinen |
| 4,529,401 A | 7/1985 | Leslie et al. |
| 4,530,696 A | 7/1985 | Bisera et al. |
| 4,542,532 A | 7/1985 | McQuilkin |
| 4,534,756 A | 8/1985 | Nelson |
| 4,550,731 A | 11/1985 | Batina et al. |
| 4,550,748 A | 11/1985 | Nunez |
| 4,557,725 A | 12/1985 | Heyne et al. |
| 4,559,037 A | 12/1985 | Franetzki et al. |
| 4,559,038 A | 12/1985 | Berg et al. |
| 4,559,044 A | 12/1985 | Robinson et al. |
| 4,561,443 A | 12/1985 | Hogrefe |
| 4,562,751 A | 1/1986 | Nason et al. |
| 4,563,179 A | 1/1986 | Sakai |
| 4,565,542 A | 1/1986 | Berg |
| 4,578,573 A | 3/1986 | Flies et al. |
| 4,596,575 A | 6/1986 | Rosenberg et al. |
| 4,597,754 A | 7/1986 | Thill et al. |
| 4,601,702 A | 7/1986 | Hudson |
| 4,606,353 A | 8/1986 | Timm |
| 4,617,014 A | 10/1986 | Cannon et al. |
| 4,623,331 A | 11/1986 | Cewers et al. |
| 4,624,661 A | 11/1986 | Arimond |
| 4,627,835 A | 12/1986 | Fenton, Jr. |
| 4,627,839 A | 12/1986 | Young |
| 4,649,499 A | 3/1987 | Sutton et al. |
| 4,650,469 A | 3/1987 | Berg et al. |
| 4,652,260 A | 3/1987 | Fenton, Jr. |
| 4,656,603 A | 4/1987 | Dunn |
| 4,658,371 A | 4/1987 | Walsh et al. |
| 4,671,792 A | 6/1987 | Borsanyi |
| 4,676,776 A | 6/1987 | Hawson |
| 4,678,408 A | 7/1987 | Nason et al. |
| 4,681,563 A | 7/1987 | Deckert et al. |
| 4,685,903 A | 8/1987 | Cable et al. |
| 4,690,673 A | 9/1987 | Blomquist |
| 4,692,147 A | 9/1987 | Duggan |
| 4,696,671 A | 9/1987 | Epstein et al. |
| 4,710,163 A | 12/1987 | Butterfield |
| 4,714,462 A | 12/1987 | DiDomenico |
| 4,722,734 A | 2/1988 | Kollin |
| D294,733 S | 3/1988 | Peterson et al. |
| 4,731,051 A | 3/1988 | Fischell |
| 4,731,058 A | 3/1988 | Doan |
| 4,731,726 A | 3/1988 | Allen, III |
| 4,739,229 A | 4/1988 | Heiler et al. |
| 4,741,732 A | 5/1988 | Granshaw et al. |
| 4,745,301 A | 5/1988 | Michalchik |
| 4,747,828 A | 5/1988 | Tseo |
| 4,754,401 A | 6/1988 | Kaczynski et al. |
| 4,756,706 A | 7/1988 | Kerns et al. |
| 4,774,029 A | 9/1988 | Poulin |
| 4,775,368 A | 10/1988 | Iwatschenko |
| 4,778,449 A | 10/1988 | Weber et al. |
| 4,785,799 A | 11/1988 | Schoon et al. |
| 4,790,816 A | 12/1988 | Sundblom et al. |
| 4,799,381 A | 1/1989 | Tromp |
| 4,808,161 A | 2/1989 | Karmen |
| 4,808,167 A | 2/1989 | Mann et al. |
| 4,809,697 A | 3/1989 | Causey, III et al. |
| 4,810,243 A | 3/1989 | Howson |
| 4,810,992 A | 3/1989 | Eventoff |
| 4,816,019 A | 3/1989 | Karmen |
| 4,818,186 A | 4/1989 | Pastrone et al. |

(56) References Cited

U.S. PATENT DOCUMENTS

| | | |
|---|---|---|
| 4,826,810 A | 5/1989 | Aoki |
| 4,832,033 A | 5/1989 | Maher et al. |
| 4,836,752 A | 6/1989 | Burkett |
| 4,838,856 A | 6/1989 | Mulreany et al. |
| 4,838,857 A | 6/1989 | Strowe et al. |
| 4,842,584 A | 6/1989 | Pastrone |
| 4,846,792 A | 7/1989 | Bobo, Jr. et al. |
| 4,847,764 A | 7/1989 | Halvorson |
| 4,847,990 A | 7/1989 | Patrick |
| 4,850,807 A | 7/1989 | Frantz |
| 4,850,972 A | 7/1989 | Schulman et al. |
| 4,852,581 A | 8/1989 | Frank |
| 4,854,324 A | 8/1989 | Hirschman et al. |
| 4,856,339 A | 8/1989 | Williams |
| 4,863,425 A | 9/1989 | Slate et al. |
| 4,869,722 A | 9/1989 | Heyman |
| 4,871,351 A | 10/1989 | Feingold |
| 4,878,896 A | 10/1989 | Garrison et al. |
| 4,882,575 A | 11/1989 | Kawahara et al. |
| 4,889,132 A | 12/1989 | Hutcheson et al. |
| 4,898,578 A | 2/1990 | Rubalcaba, Jr. |
| 4,901,221 A | 2/1990 | Kodosky et al. |
| 4,908,017 A | 3/1990 | Howson et al. |
| 4,914,568 A | 4/1990 | Kodosky et al. |
| 4,918,930 A | 4/1990 | Gaudet et al. |
| 4,919,650 A | 4/1990 | Feingold et al. |
| 4,925,444 A | 5/1990 | Orkin et al. |
| 4,927,411 A | 5/1990 | Pastrone et al. |
| 4,933,873 A | 6/1990 | Kaufman et al. |
| 4,942,514 A | 7/1990 | Miyagaki et al. |
| 4,943,279 A | 7/1990 | Samiotes et al. |
| 4,950,235 A | 8/1990 | Slate et al. |
| 4,950,244 A | 8/1990 | Fellingham et al. |
| 4,954,818 A | 9/1990 | Naking et al. |
| 4,957,690 A | 9/1990 | Fennern |
| 4,961,533 A | 10/1990 | Teller et al. |
| 4,970,664 A | 11/1990 | Kaiser |
| 4,976,151 A | 12/1990 | Morishita |
| 4,978,335 A | 12/1990 | Arthur |
| 4,979,940 A | 12/1990 | Bobo, Jr. et al. |
| 4,994,035 A | 2/1991 | Mokros |
| 4,996,511 A | 2/1991 | Ohkawa et al. |
| 5,000,739 A | 3/1991 | Kulisz et al. |
| 5,006,997 A | 4/1991 | Reich |
| 5,009,641 A | 4/1991 | Gorton |
| 5,010,473 A | 4/1991 | Jacobs |
| 5,017,059 A | 5/1991 | Davis |
| 5,032,978 A | 7/1991 | Blomquist |
| 5,034,004 A | 7/1991 | Crankshaw |
| 5,038,800 A | 8/1991 | Oba |
| 5,041,086 A | 8/1991 | Koenig et al. |
| 5,045,069 A | 9/1991 | Imparato |
| 5,047,014 A | 9/1991 | Mosebach et al. |
| 5,050,612 A | 9/1991 | Matsumura |
| 5,053,585 A | 10/1991 | Yaniger |
| 5,053,990 A | 10/1991 | Kreifels |
| 5,062,774 A | 11/1991 | Kramer et al. |
| 5,069,668 A | 12/1991 | Boydman |
| 5,074,756 A | 12/1991 | Davis |
| 5,078,682 A | 1/1992 | Miki et al. |
| 5,078,683 A | 1/1992 | Sancoff et al. |
| 5,082,014 A | 1/1992 | Olichney |
| 5,084,828 A | 1/1992 | Kaufman et al. |
| 5,087,245 A | 2/1992 | Doan |
| 5,088,983 A | 2/1992 | Burke |
| 5,096,385 A | 3/1992 | Georgi et al. |
| 5,098,262 A | 3/1992 | Wecker et al. |
| 5,098,409 A | 3/1992 | Stock |
| 5,100,380 A | 3/1992 | Epstein et al. |
| 5,103,211 A | 4/1992 | Daoud et al. |
| 5,104,374 A | 4/1992 | Bishko et al. |
| 5,111,234 A | 5/1992 | Taniguchi et al. |
| 5,115,223 A | 5/1992 | Moody |
| 5,116,312 A | 5/1992 | Blankenship et al. |
| 5,122,820 A | 6/1992 | Pagano et al. |
| 5,124,744 A | 6/1992 | Ogura et al. |
| 5,124,802 A | 6/1992 | Ito et al. |
| 5,131,816 A | 7/1992 | Brown et al. |
| 5,140,862 A | 8/1992 | Pappalardo |
| 5,153,827 A | 10/1992 | Coutre et al. |
| 5,154,700 A | 10/1992 | Danby |
| 5,155,693 A | 10/1992 | Altmayer et al. |
| 5,157,928 A | 10/1992 | Gaudlet et al. |
| 5,168,441 A | 12/1992 | Onarheim et al. |
| 5,172,698 A | 12/1992 | Stanko |
| 5,174,472 A | 12/1992 | Raque et al. |
| 5,176,004 A | 1/1993 | Gaudet |
| 5,181,910 A | 1/1993 | Scanlon |
| 5,190,442 A | 3/1993 | Jorritsma |
| 5,190,522 A | 3/1993 | Wojiciki et al. |
| 5,207,642 A | 5/1993 | Orkin et al. |
| 5,211,626 A | 5/1993 | Frank et al. |
| 5,213,573 A | 6/1993 | Hyman et al. |
| 5,217,355 A | 6/1993 | Hyman et al. |
| 5,219,327 A | 6/1993 | Okada |
| 5,221,268 A | 6/1993 | Barton et al. |
| 5,224,051 A | 6/1993 | Johnson |
| 5,230,623 A | 7/1993 | Guthrie et al. |
| 5,238,001 A | 8/1993 | Gallant et al. |
| 5,241,461 A | 8/1993 | Georges |
| 5,244,461 A | 9/1993 | Derlien |
| 5,244,463 A | 9/1993 | Cordner, Jr. et al. |
| 5,247,434 A | 9/1993 | Peterson et al. |
| 5,256,157 A | 10/1993 | Samiotes et al. |
| 5,265,431 A | 11/1993 | Gaudet et al. |
| 5,267,174 A | 11/1993 | Kaufman |
| 5,267,218 A | 11/1993 | Elbert |
| 5,291,190 A | 3/1994 | Scarola et al. |
| 5,295,062 A | 3/1994 | Fukshima |
| 5,301,301 A | 4/1994 | Kodusky et al. |
| 5,307,263 A | 4/1994 | Brown |
| 5,315,530 A | 5/1994 | Gerhardt et al. |
| 5,317,506 A | 5/1994 | Coutre et al. |
| 5,321,601 A | 6/1994 | Riedel et al. |
| 5,338,157 A | 8/1994 | Blomquist |
| 5,339,821 A | 8/1994 | Fujimoto |
| 5,350,411 A | 9/1994 | Ryan et al. |
| 5,353,316 A | 10/1994 | Scarola et al. |
| 5,354,273 A | 10/1994 | Hagen |
| 5,356,378 A | 10/1994 | Doan |
| 5,357,427 A | 10/1994 | Langen et al. |
| 5,363,482 A | 11/1994 | Victor et al. |
| 5,364,346 A | 11/1994 | Schrezenmeir |
| 5,368,562 A | 11/1994 | Blomquist et al. |
| 5,376,070 A | 12/1994 | Purvis et al. |
| 5,378,231 A | 1/1995 | Johnson et al. |
| 5,383,855 A | 1/1995 | Nicholson et al. |
| 5,386,360 A | 1/1995 | Wilson et al. |
| 5,388,202 A | 2/1995 | Squires et al. |
| 5,389,071 A | 2/1995 | Kawahara et al. |
| 5,389,078 A | 2/1995 | Zelesky et al. |
| 5,395,321 A | 3/1995 | Kawahara et al. |
| 5,400,246 A | 3/1995 | Wilson et al. |
| 5,412,400 A | 5/1995 | Takahara et al. |
| 5,429,602 A | 7/1995 | Hauser |
| 5,431,627 A | 7/1995 | Pastrone et al. |
| 5,432,709 A | 7/1995 | Vollweiler et al. |
| 5,440,585 A | 8/1995 | Patridge, III |
| 5,456,691 A | 10/1995 | Snell |
| 5,478,211 A | 12/1995 | Dominiak et al. |
| 5,479,643 A | 12/1995 | Bhaskar et al. |
| 5,481,250 A | 1/1996 | Hano |
| 5,482,446 A | 1/1996 | Williamson et al. |
| 5,485,408 A | 1/1996 | Blomquist |
| 5,531,697 A | 7/1996 | Olsen et al. |
| 5,531,698 A | 7/1996 | Olsen |
| 5,537,436 A | 7/1996 | Bottoms et al. |
| 5,558,640 A | 9/1996 | Pfeiler et al. |
| 5,569,187 A | 10/1996 | Kaiser |
| 5,573,506 A | 11/1996 | Vasko |
| 5,582,593 A | 12/1996 | Hultman |
| 5,594,786 A | 1/1997 | Chaco et al. |
| 5,598,420 A | 1/1997 | Kaufman |
| 5,616,121 A | 4/1997 | McKay |

(56) References Cited

U.S. PATENT DOCUMENTS

| | | |
|---|---|---|
| 5,626,144 A | 5/1997 | Tacklind et al. |
| 5,630,710 A | 5/1997 | Tunc et al. |
| 5,643,212 A | 7/1997 | Coutre et al. |
| 5,647,854 A | 7/1997 | Olsen et al. |
| 5,658,250 A | 8/1997 | Blomquist et al. |
| 5,658,252 A | 8/1997 | Johnson |
| 5,660,176 A | 8/1997 | Iliff |
| 5,665,065 A | 9/1997 | Colman et al. |
| 5,669,877 A | 9/1997 | Blomquist |
| 5,681,285 A | 10/1997 | Ford et al. |
| 5,685,844 A | 11/1997 | Marttila |
| 5,687,734 A | 11/1997 | Dempsey et al. |
| 5,695,473 A | 12/1997 | Olsen |
| 5,704,366 A | 1/1998 | Tacklind et al. |
| 5,706,458 A | 1/1998 | Koppolu |
| 5,717,603 A | 2/1998 | McClendon et al. |
| 5,718,562 A | 2/1998 | Lawless et al. |
| 5,719,761 A | 2/1998 | Gatti et al. |
| 5,764,159 A | 6/1998 | Neftel |
| 5,772,635 A | 6/1998 | Dastur et al. |
| 5,781,442 A | 7/1998 | Engleson et al. |
| 5,782,805 A | 7/1998 | Meinzer et al. |
| 5,788,669 A | 8/1998 | Peterson |
| 5,807,336 A | 9/1998 | Russo et al. |
| 5,810,771 A | 9/1998 | Blomquist |
| 5,814,015 A | 9/1998 | Gargano et al. |
| 5,822,715 A | 10/1998 | Worthington et al. |
| 5,857,967 A | 1/1999 | Frid et al. |
| 5,861,018 A | 1/1999 | Feierbach |
| 5,868,669 A | 2/1999 | Iliff |
| 5,871,465 A | 2/1999 | Vasko |
| 5,876,370 A | 3/1999 | Blomquist |
| 5,879,163 A | 3/1999 | Brown et al. |
| 5,885,245 A | 3/1999 | Lynch et al. |
| 5,895,371 A | 4/1999 | Levitas et al. |
| 5,897,493 A | 4/1999 | Brown |
| 5,899,855 A | 5/1999 | Brown |
| 5,913,310 A | 6/1999 | Brown |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,935,106 A | 8/1999 | Olsen |
| 5,940,801 A | 8/1999 | Brown |
| 5,956,501 A | 9/1999 | Brown |
| 5,960,403 A | 9/1999 | Brown |
| 5,966,691 A | 10/1999 | Kibre et al. |
| 5,997,476 A | 12/1999 | Brown |
| 6,012,034 A | 1/2000 | Hamparian et al. |
| 6,024,539 A | 2/2000 | Blomquist |
| 6,032,119 A | 2/2000 | Brown et al. |
| 6,077,055 A | 6/2000 | Vilks |
| 6,101,478 A | 8/2000 | Brown |
| RE36,871 E | 9/2000 | Esptein et al. |
| 6,132,416 A | 10/2000 | Broselow |
| 6,219,674 B1 | 4/2001 | Classen |
| 6,241,704 B1 | 6/2001 | Peterson et al. |
| 6,246,992 B1 | 6/2001 | Brown |
| 6,248,067 B1 | 6/2001 | Mavity et al. |
| 6,269,340 B1 | 7/2001 | Ford et al. |
| 6,406,426 B1 | 6/2002 | Reuss et al. |
| 6,422,057 B1 | 7/2002 | Anderson |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,641,533 B2 | 11/2003 | Causey, III et al. |
| 6,671,563 B1 | 12/2003 | Engelson et al. |
| 6,689,091 B2 | 2/2004 | Bui et al. |
| 6,744,350 B2 | 6/2004 | Blomquist |
| 6,749,586 B2 | 6/2004 | Vasko |
| 6,765,877 B1 | 7/2004 | Foschiano et al. |
| 6,790,198 B1 | 9/2004 | White et al. |
| 6,809,653 B1 | 10/2004 | Mann et al. |
| 6,852,104 B2 | 2/2005 | Blomquist |
| 6,872,200 B2 | 3/2005 | Mann et al. |
| 6,903,743 B2 | 6/2005 | Ng |
| 6,904,434 B1 | 6/2005 | Wallach et al. |
| 6,936,029 B2 | 8/2005 | Mann et al. |
| 6,956,572 B2 | 10/2005 | Zaleski |
| 6,979,326 B2 | 12/2005 | Mann et al. |
| 6,997,920 B2 | 2/2006 | Mann et al. |
| 6,999,854 B2 | 2/2006 | Roth |
| 7,025,743 B2 | 4/2006 | Mann et al. |
| 7,033,338 B2 | 4/2006 | Vilks et al. |
| 7,036,089 B2 | 4/2006 | Bauer |
| 7,041,082 B2 | 5/2006 | Blomquist et al. |
| 7,042,643 B2 | 5/2006 | Miles |
| 7,098,803 B2 | 8/2006 | Mann et al. |
| 7,103,578 B2 | 9/2006 | Beck et al. |
| 7,109,878 B2 | 9/2006 | Mann et al. |
| 7,233,781 B2 | 6/2007 | Hunter et al. |
| 7,300,418 B2 | 11/2007 | Zaleski |
| 7,324,012 B2 | 1/2008 | Mann et al. |
| 7,347,836 B2 | 3/2008 | Peterson |
| D570,363 S | 6/2008 | Ulm et al. |
| D576,175 S | 9/2008 | Onodera |
| D580,948 S | 11/2008 | Tomizawa et al. |
| 7,454,314 B2 | 11/2008 | Holland |
| D586,351 S | 2/2009 | Gelman et al. |
| D586,357 S | 2/2009 | Janinski |
| D604,741 S | 11/2009 | DeBelser et al. |
| 7,647,237 B2 | 1/2010 | Malave et al. |
| 7,654,976 B2 | 2/2010 | Peterson et al. |
| 7,689,939 B1 | 3/2010 | Becker |
| 7,708,717 B2 | 5/2010 | Estes et al. |
| 7,789,859 B2 | 9/2010 | Estes et al. |
| 7,794,427 B2 | 9/2010 | Estes et al. |
| 7,895,527 B2 | 2/2011 | Zaleski |
| 7,912,674 B2 | 3/2011 | Clark |
| 8,020,564 B2 | 9/2011 | Batch |
| 8,065,161 B2 | 11/2011 | Howard |
| 8,149,131 B2 | 4/2012 | Blomquist |
| 8,182,461 B2 | 5/2012 | Pope |
| 8,209,060 B2 | 6/2012 | Ledford |
| 8,234,128 B2 | 7/2012 | Martucci et al. |
| 8,250,483 B2 | 8/2012 | Blomquist |
| 8,313,433 B2 | 11/2012 | Cohen |
| 8,346,399 B2 | 1/2013 | Blomquist |
| 8,435,206 B2 | 5/2013 | Evans et al. |
| 8,504,179 B2 | 8/2013 | Blomquist |
| 8,768,717 B2 | 7/2014 | Blomquist |
| 8,858,526 B2 | 10/2014 | Blomquist |
| 8,965,707 B2 | 2/2015 | Blomquist |
| 8,974,406 B2 | 3/2015 | Evans et al. |
| 9,132,230 B2 | 9/2015 | Blomquist |
| 9,135,393 B1 | 9/2015 | Blomquist |
| 9,192,712 B2 | 11/2015 | DeBelser et al. |
| 9,501,949 B2 | 11/2016 | Hansen et al. |
| 2001/0031944 A1 | 10/2001 | Peterson et al. |
| 2002/0029776 A1 | 3/2002 | Blomquist |
| 2002/0077852 A1 | 6/2002 | Ford |
| 2002/0077863 A1 | 6/2002 | Rutledge |
| 2002/0107476 A1 | 8/2002 | Mann et al. |
| 2002/0151804 A1 | 10/2002 | O'Mahony et al. |
| 2002/0183693 A1 | 12/2002 | Peterson et al. |
| 2002/0193679 A1 | 12/2002 | Malave et al. |
| 2003/0011646 A1 | 1/2003 | Levine et al. |
| 2003/0060765 A1 | 3/2003 | Campbell et al. |
| 2003/0069650 A1 | 4/2003 | Karmiy et al. |
| 2003/0114836 A1 | 6/2003 | Estes et al. |
| 2003/0139701 A1 | 7/2003 | White et al. |
| 2003/0140928 A1 | 7/2003 | Bui |
| 2003/0144880 A1 | 7/2003 | Kaivan et al. |
| 2003/0145053 A1 | 7/2003 | Bodin |
| 2003/0163088 A1 | 8/2003 | Blomquist |
| 2003/0163223 A1 | 8/2003 | Blomquist |
| 2003/0163789 A1 | 8/2003 | Blomquist |
| 2003/0173408 A1 | 9/2003 | Mosher et al. |
| 2003/0204413 A1 | 10/2003 | Riff |
| 2003/0204415 A1 | 10/2003 | Knowlton |
| 2003/0204416 A1 | 10/2003 | Sayeh et al. |
| 2003/0212364 A1 | 11/2003 | Mann |
| 2003/0212379 A1 | 11/2003 | Bylund et al. |

(56) References Cited

U.S. PATENT DOCUMENTS

| | | |
|---|---|---|
| 2004/0010425 A1 | 1/2004 | Wilkes et al. |
| 2004/0065321 A1 | 4/2004 | Stenzler |
| 2004/0073095 A1 | 4/2004 | Causey, III et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172301 A1 | 9/2004 | Mihai et al. |
| 2004/0172302 A1 | 9/2004 | Martucci et al. |
| 2004/0176984 A1 | 9/2004 | White et al. |
| 2004/0249673 A1 | 12/2004 | Smith |
| 2005/0001797 A1 | 1/2005 | Miller |
| 2005/0010258 A1 | 1/2005 | Peterson et al. |
| 2005/0055242 A1 | 3/2005 | Bello et al. |
| 2005/0065817 A1 | 3/2005 | Mihai et al. |
| 2005/0107923 A1 | 5/2005 | Vanderveen |
| 2005/0119914 A1 | 6/2005 | Batch |
| 2005/0137530 A1 | 6/2005 | Campbell et al. |
| 2005/0143864 A1 | 6/2005 | Blomquist |
| 2005/0144182 A1 | 6/2005 | Boris et al. |
| 2005/0030164 A1 | 8/2005 | Mann et al. |
| 2005/0077096 A1 | 8/2005 | Bollish |
| 2005/0171513 A1 | 8/2005 | Mann et al. |
| 2005/0171815 A1 | 8/2005 | Vanderveen |
| 2005/0177395 A1 | 8/2005 | Blomquist |
| 2005/0246416 A1 | 11/2005 | Blomquist |
| 2006/0000480 A1 | 1/2006 | Broselow |
| 2006/0001550 A1 | 1/2006 | Mann et al. |
| 2006/0026205 A1 | 2/2006 | Butterfield |
| 2006/0031094 A1 | 2/2006 | Cohen et al. |
| 2006/0041222 A1 | 2/2006 | Dewing et al. |
| 2006/0079768 A1 | 4/2006 | Small et al. |
| 2006/0089539 A1 | 4/2006 | Miodownik et al. |
| 2006/0097991 A1 | 5/2006 | Hotelling |
| 2006/0132292 A1 | 6/2006 | Blomquist |
| 2006/0137696 A1 | 6/2006 | Broselow |
| 2006/0202859 A1 | 9/2006 | Mastrototaro et al. |
| 2006/0229557 A1 | 10/2006 | Fathallah et al. |
| 2006/0258985 A1* | 11/2006 | Russell ............ A61M 5/14212 604/151 |
| 2006/0264249 A1 | 11/2006 | Scheer |
| 2007/0073872 A1* | 3/2007 | Wille ................. G06Q 20/346 709/224 |
| 2007/0094046 A1 | 4/2007 | Cobbs et al. |
| 2007/0156033 A1 | 7/2007 | Causey, III et al. |
| 2007/0213657 A1 | 9/2007 | Jennewine et al. |
| 2007/0233520 A1 | 10/2007 | Wehba et al. |
| 2007/0255322 A1 | 11/2007 | Gerber et al. |
| 2007/0260126 A1 | 11/2007 | Haumann |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0033402 A1 | 2/2008 | Blomquist |
| 2008/0033749 A1 | 2/2008 | Blomquist |
| 2008/0034323 A1 | 2/2008 | Blomquist |
| 2008/0065007 A1 | 3/2008 | Peterson et al. |
| 2008/0065016 A1 | 3/2008 | Peterson et al. |
| 2008/0091466 A1 | 4/2008 | Butler |
| 2008/0126969 A1 | 5/2008 | Blomquist |
| 2008/0132844 A1 | 6/2008 | Peterson et al. |
| 2008/0243548 A1 | 10/2008 | Cafer |
| 2008/0300534 A1 | 12/2008 | Blomquist |
| 2009/0156991 A1 | 6/2009 | Roberts et al. |
| 2009/0157695 A1 | 6/2009 | Roberts |
| 2009/0177180 A1 | 7/2009 | Rubalcaba et al. |
| 2009/0270810 A1 | 10/2009 | DeBelser |
| 2009/0275886 A1 | 11/2009 | Blomquist et al. |
| 2010/0020064 A1 | 1/2010 | Roosendaal et al. |
| 2010/0057488 A1 | 3/2010 | Broselow |
| 2010/0121654 A1 | 5/2010 | Portnoy |
| 2010/0228222 A1 | 9/2010 | Williams |
| 2011/0004071 A1 | 1/2011 | Faiola |
| 2011/0145012 A1 | 6/2011 | Nightingale |
| 2011/0193788 A1 | 8/2011 | King |
| 2011/0264462 A1 | 10/2011 | Broselow |
| 2012/0013625 A1 | 1/2012 | Blomquist et al. |
| 2012/0013802 A1 | 1/2012 | Blomquist et al. |
| 2012/0065990 A1 | 3/2012 | Howard |
| 2012/0131507 A1 | 5/2012 | Sparandara |
| 2012/0172802 A1 | 7/2012 | Blomquist |
| 2012/0278099 A1 | 11/2012 | Kelly |
| 2012/0323212 A1* | 12/2012 | Murphy ................. A61M 5/00 604/500 |
| 2013/0012878 A1 | 1/2013 | Blomquist |
| 2013/0012879 A1 | 1/2013 | Debelser et al. |
| 2013/0012880 A1 | 1/2013 | Blomquist |
| 2013/0015980 A1 | 1/2013 | Evans |
| 2013/0018315 A1 | 1/2013 | Blomquist |
| 2013/0131630 A1 | 5/2013 | Blomquist |
| 2014/0094744 A1 | 4/2014 | Blomquist |
| 2014/0094764 A1 | 4/2014 | Blomquist |
| 2014/0095485 A1 | 4/2014 | Blomquist |
| 2014/0095499 A1 | 4/2014 | Blomquist |
| 2014/0180711 A1* | 6/2014 | Kamen ................. G06Q 10/06 705/2 |
| 2015/0154369 A1 | 6/2015 | Blomquist |
| 2015/0161354 A1 | 6/2015 | Blomquist |
| 2015/0367065 A1 | 12/2015 | Adams et al. |
| 2016/0000994 A1 | 1/2016 | Blomquist |
| 2016/0147978 A1 | 5/2016 | Adams et al. |

FOREIGN PATENT DOCUMENTS

| | | |
|---|---|---|
| CA | 2554903 | 4/2005 |
| CA | 2607297 | 11/2006 |
| CA | 2647816 | 11/2007 |
| CA | 2659494 | 2/2008 |
| CH | 665955 | 6/1988 |
| EP | 0069350 | 1/1983 |
| EP | 0078645 | 5/1983 |
| EP | 0183351 | 6/1986 |
| EP | 0188288 | 7/1986 |
| EP | 0221005 | 5/1987 |
| EP | 0233115 | 8/1987 |
| EP | 319272 | 6/1989 |
| EP | 0328162 | 8/1989 |
| EP | 0384155 | 8/1990 |
| EP | 408483 | 1/1991 |
| EP | 0497041 | 8/1992 |
| EP | 503670 | 9/1992 |
| EP | 0371507 | 3/1993 |
| EP | 551088 | 7/1993 |
| EP | 0806738 | 11/1997 |
| EP | 0952541 | 10/1999 |
| EP | 1587017 | 10/2005 |
| EP | 1647291 | 4/2006 |
| FR | 2603488 | 3/1988 |
| GB | 2039083 | 7/1980 |
| GB | 2262452 | 6/1993 |
| GB | 2312055 | 10/1997 |
| JP | 409192218 | 7/1997 |
| JP | 2002291706 | 10/2002 |
| KR | 10-2010-0126598 A | 12/2010 |
| WO | WO8703814 | 7/1987 |
| WO | WO8707161 | 12/1987 |
| WO | WO91/16609 | 10/1991 |
| WO | WO92/08647 | 5/1992 |
| WO | WO92/15439 | 9/1992 |
| WO | WO94/05355 | 3/1994 |
| WO | WO94/08647 | 4/1994 |
| WO | WO 8403218 | 8/1994 |
| WO | WO95/02426 | 1/1995 |
| WO | WO95/25893 | 9/1995 |
| WO | WO95/28190 | 10/1995 |
| WO | WO96/03168 | 2/1996 |
| WO | WO1996013790 | 5/1996 |
| WO | WO96/20745 | 7/1996 |
| WO | WO96/36389 | 11/1996 |
| WO | WO97/25083 | 7/1997 |
| WO | WO97/15227 | 4/1998 |
| WO | WO98/20439 | 5/1998 |
| WO | WO98/24358 | 6/1998 |
| WO | WO98/42407 | 10/1998 |
| WO | WO98/59487 | 12/1998 |

(56) References Cited

FOREIGN PATENT DOCUMENTS

| WO | WO99/08183 | 2/1999 |
|---|---|---|
| WO | WO99/10801 | 3/1999 |
| WO | WO99/18532 | 4/1999 |
| WO | WO99/22236 | 5/1999 |
| WO | WO0045696 | 8/2000 |
| WO | WO0048112 | 8/2000 |
| WO | WO 0152727 | 7/2001 |
| WO | WO02/11049 | 2/2002 |
| WO | WO03/053503 | 7/2003 |
| WO | WO03/094075 | 11/2003 |
| WO | WO 2005/056083 | 6/2005 |
| WO | WO 2005/083619 | 9/2005 |
| WO | WO2006/023636 | 3/2006 |
| WO | WO 2006/073400 | 7/2006 |
| WO | WO 2006/122322 | 11/2006 |
| WO | WO2007/101260 | 9/2007 |
| WO | WO2008/019013 | 2/2008 |
| WO | WO2008/019014 | 2/2008 |
| WO | WO2008/019015 | 2/2008 |
| WO | WO2008016621 | 2/2008 |
| WO | WO2008/048587 | 4/2008 |
| WO | WO2008/019016 | 11/2008 |
| WO | WO2009/0135108 | 11/2009 |
| WO | WO 2012/093163 | 7/2012 |
| WO | WO 2012/166434 | 12/2012 |

OTHER PUBLICATIONS

Institute for Safe Medication Practices, *Proceedings from the ISMP Summit on the Use of Smart Infusion Pumps: Guidelines for Safe Implementation and Use*, © 2009, 19 pages.

Vanderveen, Tim, *A Decade of "Smart" Infusion Pumps*, Feb. 27, 2012, 2 pages.

Huang, Zifang, *Prediction of Uterine Contractions Using Knowledge-Assisted Sequential Pattern Analysis*, IEEE © 2011, 8 pages.

"A Programable Infusion Pump Controller," 30th Annual Conference on Engineering in Medicine and Biology, Nov. 5-9, 1977 in Los Angeles, California, 11 pages.

"A Programmable Infusion Pump Controller," 30th Annual Conference on Engineering in Medicine and Biology, Nov. 5-9, 1977 in Los Angeles, California, 11 pages.

"Ally™ Ambulatory Frug Infusion System", Q-Life Systems Inc., 3 pages, as submitted Jun. 29, 1988 in U.S. Appl. No. 08/868,913.

"IV700 Service Manual." Valleylab, Inc. Boulder Colorado; Sep. 1988.

"Product Overview, Verifuse Ambulatory Infusion Pump." Block Medical Inc, dated Sep. 1990, 4 pages.

510 (k) Registration Documents for Registration of K863997 (1986).

510 (k) Registration Documents for Registration of K87022 and K871728 (1987).

A Semi-closed loop computer-assisted insulin infusion system, Donald J. Chisholm, Edward W. Kraegen, David J. Bell and David R. Chipps, The Medical Journal of Australia, Dec. 08/22, 1984. pp. 13-17.

A Semi-Closed Loop Computer-Assisted Insulin Infusion System. Hospital use for Control of Diabetes in Patients, Chisholm DJ, Kraegan EW, Bell DJ, Chipps DR, Med J. Aust. Dec. 8-22, 1984;141(12-13):784-9.

A Simulation Study on a Self-Tuning Portable Controller of Blood Glucose. Brunetti P, Cobelli C, Cruciani P, Fabietti PG, Filippucci F, Santeusanio F, Sarti E. Medical Pathology Institute, Bioengineering Laboratory. University of Perugia, Italy. Int. J. ArtifOrgans. Jan. 1993; 16(1):51-7.

A Standard Microcomputer Linked to a Volume-Controlled Infusion Pump for Patient-Controlled Analgesia Research, Journal of Medical Engineering and Technology, G.W.A. Gillies, G.N.C. Kenny and C.S. McArdle, vol. 10, No. 2, Mar./Apr. 1986. pp. 55-57.

Abbot Laboratories Blue Line System Life Care® Model 4 Series System brochure, copyright 1990, 16 pages.

Abbot Literature, 37 pages, as submitted Jun. 29, 1988 in U.S. Appl. No. 08/868,913.

Advertisement from HERCO, Are Control Rooms Obsolete? Dated Mar. 1971, 1 page and Mar. 1972, 1 page.

Answer and Counterclaims of Smiths Medical Md. Inc. (Exhibits 1-5); C.A. 03-776, *Medtronic Minimed, Inc.* v. *Deltec Inc., Smiths Group North America, Inc. and Smiths Group Pic*. Nov. 17, 2003.

Application an File History for U.S. Appl. No. 11/499,248, filed Aug. 3, 2006, inventor Blomquist.

Application and File History for U.S. Appl. No. 11/499,240, filed Aug. 3, 2006, inventor Blomquist.

Application and File History for U.S. Appl. No. 11/702,925, filed Feb. 5, 2007 inventors Evans et al.

Application and File History for U.S. Appl. No. 13/620,031, filed Sep. 14, 2012 inventor Blomquist.

Application and File History for U.S. Appl. No. 13/619,964, filed Sep. 14, 2012 inventors Evans et al.

Application and File History for U.S. Appl. No. 14/811,035 dated Jul. 28, 2015, inventors Adams et al.

Application and File History for U.S. Appl. No. 14/851,322, filed Sep. 11, 2015 inventor Blomquist.

Article by McMorris et al., "Are Process Control Rooms Obsolete? ", Control Engineering dated Jul. 1971, pp. 42-47.

Australian Examination Report No. 3 for Australian Application No. 2007282068 dated Jun. 4, 2013.

Australian Examination Report No. 3 for Australian Application No. 2007282068 dated Jun. 17, 2013.

Australian Examiner's first report on Australian Application No. 2007282068 dated May 10, 2012.

Australian Office Action for Application No. 2004296794 dated Dec. 3, 2009.

Australian Patent Examination Report No. 2 for Australian Application No. 2007282068 dated Dec. 17, 2012.

Australian Patent Examination Report No. 2 for Australian Application No. 2007282070 dated Nov. 2, 2012.

Automated Patient Care Following Cardiac Surgery. Nicholas T. Kouchoukos; Louis B. Sheppard; John W. Kirklin, Cardiovascular Clinics, Bol. 3, pp. 110-120, 1971.

Baxter Literature for Flo-Guard® 6201 Volumetric Infusion Pump, Copyright 1992, 2 pages.

Baxter Literature for MultiPlex™ Series 100 Fluid Management System, 4 pages, as submitted Jun. 29, 1988 in U.S. Appl. No. 08/868,913.

Bedder, M. et al., "Cost Analysis of Two Implantable Narcotic Delivery Systems," Journal of Pain and Symptom Management. vol. 6, No. 6, Aug. 1991. pp. 368-373.

Bio Tek Instruments, Inc. Products Catalog. 32 pages. Apr. 1992.

Blade-Citizen, "Entrepeneur takes Aim at Home Health Care Market," Dec. 31, 1989, 2 pages.

Block Medical: Growing with Home Infusion Therapy, In Vivio, The Business and Medicine Report, Apr. 1991, 3 pages.

Canadian Office Action for Canadian Application No. 2,659,485 dated Aug. 22, 2013.

Canadian Office Action for Canadian Application No. 2,659,485 dated Mar. 27, 2014.

Canadian Office Action for Canadian Application No. 2,659,494 dated May 12, 2014.

Canadian Office Action for Canadian Application No. 2,659,494 dated Apr. 6, 2017.

Canadian Office Action for Canadian Application No. 2,659,616 dated Jun. 6, 2014.

Canadian Office Action for Canadian Application No. 2,659,618 dated Jun. 16, 2014.

Canadian Office Action for Canadian Application No. 2,659,629 dated May 8, 2014.

Chinese Office Action for Chinese Application No. 201480006387.X dated Apr. 17, 2018.

Communication (Reply to Applicant's Arguments) from Canadian Patent Office for Canadian Application No. 2,659,618 dated Apr. 13, 2015.

Complaint for Patent Infringement (Exhibits 1-3); C.A. No. 03-776, *Medtronic Minimed, Inc.* v. *Deltec Inc., and Smiths Medical Ltd*. Aug. 5, 2003.

(56) References Cited

OTHER PUBLICATIONS

Computerized Continuous Infusion of Intravenous Anesthetic Drugs During Pediatric Cardiac Surgery; Kern FH, Ungerleider RM, Jacobs JR, Boyd JL 3rd, Reves JG, Goodman D. Greeley WJ; Department of Anesthesiology, Duke Heart Center, Duke University Medical Center, Durham, North Carolina, Anesth Analg. Apr. 1991; 72(4): 487-92.
Decision of Refusal for Japanese Application No. 2006-542752 dispatch date Jul. 4, 2011.
Decision of Refusal for Japanese Application No. 2006-554321 dispatch date Apr. 18, 2011.
Decision to refuse European Application for European Application No. 07836389.2-2201 dated Dec. 18, 2012.
Decision to refuse European Application for European Application No. 07836379.3-2201 dated Dec. 18, 2012.
Declaration of Anthony C. Roth in Support of Defendant—Counterclaim Plantiff Smiths Medical Md, Inc. 'S Response Brief to Medtronic Minimed, Inc.'S Claim Construction Brief of U.S. Pat. No. 6,241,704 (Exhibits A-H); C.A. No. 03-776, *Medtronic Minimed Inc.* v. *Smith Medical Md, Inc.* Feb. 25, 2005.
Declaration of Anthony C. Roth in Support of Defendant—Counterclaim Plaintiff Smiths Medical Md, Inc. 'S Brief in Opposition ot Medtronic Minimed Inc. 'S Motion for Summary Judgment of invalidity of claims 6 and 11 of Smiths Medical Inc. 'S U.S. Pat. No. 6,241,704 (Exhibits 1-7); C,A, No. 03-7769, *Medtronic Minimed Inc.* v. *Smiths Medical Md. Inc.* Feb. 28, 2005.
Declaration of non-establishment of ISR for International Application No. PCT/US2009/042494 dated Jan. 5, 2010.
Defendant Smiths Medical Md, Inc. 'S Brief in Opposition to Medtronic Minimed, Inc 'S Motion for Summary Judgment of Invalidity of Claims 6 and 11 of Smiths Medical Inc. 'S U.S. Pat. No. 6,241,704; C.A. No. 03-776, *Medtronic Minimed, Inc.* v. *Smiths Medical Md. Inc.* Feb. 28, 2005.
Defendant Smiths Medical Md. Inc. S. Answering Brief Responding to Medtronic Minimed Inc.'S Claim Contruction Brief for U.S. Pat. No. 6,241,704, C.A. No. 03-776, *Medtronic Minimed Inc.* v. *Smiths Medical Md. Inc.* Feb. 25, 2005.
Dehne, T., "PC-Based Data Acquisition and Intrumentation,"Analytical Chemistry, vol. 62, No. 9, May 1, 1990. pp. 565A, 566A, 568A, 570A, 571A, 572A.
Dertouzos, M., "Communications, Computers & Net-works," Scietific American Sep. 1991, pp. 62-69.
Designing the User Interface, Ben Schneiderman, Chapter 5 Direct Manipulation, Oct. 1993, 56 pages.
Devices for Insulin Administration, Jean-Louis Selam, MD and M. Arthur Charles, MD, PhD., Diabetes Care, vol. 13, No. 9, Sep. 1990. pp. 955-979.
Effective Control of Blood Pressure by Computerized Infusion of Sodium Nitroprusside, R.V. Calfee, J.J. Hammond, W.M. Kirkendall, Clinical Research, vol. 25, 1977.
Electronics Feb. 1990 article entitled "Who Will Dominate the Desktop in the '90's?", 3 pages.
European Office Action for European Application No. 05713999 dated Oct. 30, 2009.
European Office Action for European Application No. 07797060 dated Jul. 3, 2009.
European Office Action for European Application No. 07797060 dated Feb. 9, 2010.
European Office Action for European Application No. 07797060 dated Dec. 8, 2010.
European Office Communication for European Application No. 07810949.3-1662 dated Feb. 25, 2013.
European Office Communication for European Application No. 07836379.3-2201/2050037 dated Jul. 18, 2012.
European Supplementary Partial EP Search Report for EP Application No. EP14743307 dated May 16, 2017.
Examination Report No. 1 for Australian Application No. 2014209383 date of report Jul. 20, 2017.
Examination Report No. 2 for Australian Application No. 2014209383 dated Feb. 15, 2018.

Examiner's first report for Australian patent application No. 2007282071 dated Jul. 11, 2011.
Examiner's first report on Australian patent application No. 2007282069 dated Jul. 11, 2011.
Examiner's first report on Australian patent application No. 2007281512 dated Jul. 4, 2011.
Examiner's first report on No. 4 on Australian patent application No. 2005216321 dated Aug. 25, 2011.
Examiner's report No. 2 on patent application No. 2005216321 by Smiths Medical ASD, Inc. dated Jan. 7, 2011. Australian Government IP.
Examiner's report No. 3 on patent application No. 2005216321 by Smiths Medical ASD Inc. dated Apr. 20, 2011, Australian Government IP.
Examiner's first report on patent application No. 2004296794 by Smiths Medical ASD, Inc. dated Dec. 3, 2009. Australian Government IP.
Examiner's first report on patent application No. 2005216321 by Smiths Medical ASD, INC dated Nov. 26, 2009.
Expert Report of Jack Goldberg on behalf of Plaintiff Medtronic Minimed Pursuant to Fed R. Civ. P. 26(A)(2) (Exhibits A-F); C.A. No. 03-776, *Medtronic Minimed Inc.* v. *Smiths Medical Md. Inc.* Executed Dec. 15, 2004.
Expert Response of Anthony Storace on behalf of Defendant Counterclaimant Smiths Medical Md., Inc. to the Expert Report Submitted by jack Goldberg on behlaf of Plaintiff Medtronic Minimed (Exhibits B-J); C.A. No. 03-776, *Medtronic Minimed Inc.* v. *Smiths Medical Md, Inc.* Jan. 14, 2005.
First Amended Complaint for Patent Infringement (Exhibits 1-3); C.A. No. 03-776, *Medtronic Minimed, Inc.* v. *Deltec Inc. Smiths Group North America Inc. and Smiths Medical Ltd*. Nov. 3, 2003.
Fundamentals of Interactive Computer Graphics, Foley et al., Mar. 1993, pp. 10, 11, 29-35.
Greg Sancoff. San Diego Executive, "A Better Mousetrap," Sep. 1989, 4 pages.
Health Devices, ECRI A Nonprofit Agency, Dec. 1989, vol. 18 No. 12.
Health Devices, ECRI A Nonprofit Agency, Dec. 1991, vol. 20 No. 12.
Health Devices, ECRI A Nonprofit Agency, Sep. 1991, vol. 20, No. 9.
Health Devices, ECRI A Nonprofit Agency, vol. 17 No. 12, Dec. 1988.
Health Devices, ECRI A Nonprofit Agency, vol. 19 Nos. 3-4, Mar.-Apr. 1989.
Hypertensive Crisis Managed by Computer-Controlled Infusion of Sodium Nitroprusside; A Model for the Closed-Loop Administration of Short-Acting Vasoactive Agents. Jeremy J. Hammond, Walter M. Kirkdendall, Richard V. Calfee, Comupters and Biomedical Research, vol. 12, pp. 97-108, 1979.
IMED 980 Volumetric Infusion Pump Operator's Manual. 1992.
IMED STATUS Infusion Management System literature, 6 pages, as submitted Jun. 29, 1988 in U.S. Appl. No. 08/868,913.
Improving Acute Care Use of Medical Device Data, Robert J. Kennelly, Chair, IEEE 1073 "Standard for Medical Device Communications" Committee, Eden Shores Consulting. 1992.
Instruction Manual entitled "Quick Start for Speakerphone XT SVD", copyright 1996.
Intel® document entitled, 28F001BX-T/28F001BX-B 1M(128Kx8) CMOS Flash Memory, dated Mar. 1991, 28 pages.
International Search Report and Written Opinion for International Application No. PCT/US2004/040397 dated Feb. 7, 2006.
International Search Report and Written Opinion for International Application No. PCT/US2007/017138 dated Nov. 20, 2007.
International Search Report and Written Opinion for PCT/US2007/017120 dated Jan. 25, 2008.
International Search Report for International Application No. PCT/US94/07582 dated Oct. 28, 1994.
International Search Report for International Application No. PCT/US2007/017122 dated Feb. 19, 2008.
International Search Report for International Application No. PCT/US2005/005829 dated Nov. 10, 2005.

(56) References Cited

OTHER PUBLICATIONS

International Search Report for International Application No. PCT/US2007/017123 dated Jan. 25, 2008.
International Search Report for International Application No. PCT/US2007/017133 dated May 8, 2008.
International Search Report for International Application No. PCT/US2007/022051 dated Mar. 7, 2008.
Intravenous propofol anaesthesia using a computerized infusion system, M. White and G.N.C. Kenny, Anaesthesia, 1990, vol. 45, pp. 204-209.
Invitation to Pay Additional Fees with Partial International Search for International Application No. PCT/US2007/017133 dated Feb. 27, 2008.
Joint Claim Construction Statement (Exhibits 1-2); C.A. No. 03-776, *Medtronic Minimed, Inc.* v. *Smiths Medical Md, Inc.* Certificate of service Feb. 4, 2005.
LabVIEW® User Manual, Jan. 1990 Edition, cover page and pp. 2-1 through 2-36.
Lahti W. et al., "Byte", pp. 311-318, Nov. 1990. "Store Data in a Flash".
Linkens et al., Computer Control Systems and Pharmacological Drug Administration: A Survey, Journal of Medical Engineering & Technology, vol. 14, No. 2, Mar./Apr. 1990, pp. 41-54.
M68HC11 E Series, HCMOS Microcontroller Unit, Motorola, Inc. 1993, 1996.
McCarthy, LH, Software Simulates Instrumentation Systems, Design News, May 21, 1990, pp. 72-73.
Medtronic MiniMed Paradigm Link Owner's Guide, BD Logic, 2003.
Medtronic Minimed's Reply Brief in Support of it's Motion for Summary Judgment of Non-Infringement of Claims 6 and 11 of Smiths '704 Patent (Exhibits A-B), *Medtroni Minimed Inc.* v. *Smith Medical Md, Inc.* Mar. 4, 2005.
Medtronic Minimed's Reply Brief in Support of its Motion for Sumamry Judgment of Invalidilty of Claims 6 and 11 of Smiths '704 Patent (Exhibits A-B); C.A. No. 03-776, *Medtronic Minimed Inc.* v. *Smiths Medical MD, Inc.* Mar. 4, 2005.
Memorandum Opinion (Summary Judgment of Infringement of U.S. Pat. No. 5,665,065 and U.S. Pat. No. 6,554,798), C.A. No. 03-776, *Medtronic Minimed Inc.* v. *Smiths Medical Md. Inc.* Jun. 16, 2005.
Memorandum Opinion: C.A. No. 03-776, *Medtronic Minimed, Inc.* v. *Smiths Medical Md. Inc.* Jun. 1, 2005.
Merritt, "Wireless Hospital Health Care Products on the Upswing". Jan. 7, 2004.
Model 929 Computer Controlled Volumetric Infusion Pump Operating Instructions imed® as submitted Feb. 28, 2008 in U.S. Appl. No. 11/981,788.
National Instruments' 1991 catalog entitled "IEEE-488 and VXIbus Control, Data Acquisition, and Analysis," cover page and pp. 1-1 through 1-13, 1-38, 4-68 and 4-69.
National Instruments Document entitled "Scientific Data Analysis," 16 pages, as submitted Jun. 29, 1988 in U.S. Appl. No. 08/868,913.
National Instruments Instrumentation Newsletter, Aug. 1990, 20 pages. vol. 2, No. 3.
National Instruments Instrumentation Newsletter, Feb. 1991, 20 pages. vol. 3, No. 1.
National Instruments Instrumentation Newsletter, May 1990, 18 pages. vol. 2, No. 2.
National Instruments Instrumentation Newsletter, Nov. 1990, 16 pages. vol. 2, No. 4.
National Instruments Lab Windows 1.2 materials dated Oct. 1989, 5 pages.
National Instruments Lab Windows 2.0 materials, 6 pages, as submitted Jun. 29, 1988 in U.S. Appl. No. 08/868,913.
Notice of Acceptance for Australian Application No. 2007282068 dated Feb. 11, 2014.
Notice of Acceptance for Australian Application No. 2007282070 dated Oct. 3, 2013.
Notice of First Office Action for CN Application No. 201480006387.X dated Dec. 29, 2016. Translation provided.
Notice of Reasons for Rejection for JP Application No. 2015-555273 dated Dec. 5, 2017.
Notification of Reasons for Refusal for Japanese Patent Application No. 2006-542752 dated Jun. 23, 2010.
Notification of Reasons for Refusal for Japanese Patent Application No. 2006-554321 dispatch date Apr. 19, 2010.
Opening Brief in Support of Defendant Smiths Medical, Inc.'S Propsed Claim Contructions for U.S. Pat. No. 6,241,704; U.S. Pat. No. 6,554,065 and U.S. Pat. No. 6,554,798 (Exhibits 1-20); C.A. No. 03-776, *Medtronic Minimed, Inc.* v. *Smiths Medical Md, Inc.* Feb. 4, 2005.
Operator's Manual for a CADD-Micro® Ambulatory Infusion Pump Model 5900, front cover and pp. ii-vi and 1-84, copyright 1993.
Operator's Manual for a CADD-Micro™ Ambulatroy Infusion Pump Model 5400, front cover and pp. ii-vi, pp. 1-55 and two back cover pages, copyright 1990.
Operator's Manual, Gemini® PC-1 Volumetric Infusion Pump/Controller imed® Aug. 16, 1990.
Order: C.A. No. 03-776; *Medtronic Minimed Inc.* v. *Smiths Medical Md. Inc.* Jun. 1, 2005.
Pain Control Devices Gaining Acceptance, Will Expand-Analgesic Delivery Devices—Industry Overview, http://www.findarticles.com/articles/mi_m3498/is_n5_v55/ai_12257770, Sep. 29, 2004.
Patient-controlled Portable Insulin Infusion Pump in Diabetes, Jergen Bojsen, Thorsten Deckert, Klaus Kelendorf, and Birthe Lerup, Diabetes vol. 28 Nov. 1979. Cover page and pp. 974-979.
Peter Lord et al., "MinMed Technologies Programmable Implantable Infusion System," pp. 66-91, from Annals of the New York Academy of Sciences, Neurilogical Applications of Implanted Drug Pumps, Copyright 1988.
Principles and Guidelines in Software User Interface Design, Deborah J. Mayhew, Chapter 9 Dialog Sryles: Direct Manipulation, copyright 1992, 17 pages.
Provider® One Instruction Manual, Pancretec, Inc. as submitted on May 18, 1998 in U.S. Appl. No. 08/782,486.
Range Filter Slider Control in Micosoft Excel—Clearly and Simply. Jan. 21, 2013. https://web-beta.archive.org/web/20130121145123/http"//www.cleralyandsimply.com/slearly_and_simply/2011/03range-filter-slider-control-in-microsoft-excel.html retrieved on May 3, 2017.
Second Office Action for Chinese Patent Application No. 201480006387.X dated Sep. 25, 2017. Translation Provided.
Sheppard, L.C., Computerbased Clinical Systems: Automation and Intergration, 39th Annual Conference on Engineering in Medicine and Biology, Baltimore, Maryland, Sep. 13-16, 1986, pp. 73-75.
Singapore Written Opinion for Singapore Application No. 11201505142T dated Mar. 4, 2016.
Steinfeld, Is Embedded Going Net-Crazy?? A Response. Internet Article Mar. 29, 2001.
Steinfeld, Internet-Appliance Technology Automates Test Equipment. pp. 157-169. Oct. 12, 2000.
The Orange County Register No. 21, 1991 article entitled "Portable TV frees patients," 1 page.
The P1073 Medical Information Bus, David F. Franklin and David V. Ostler (Oct. 1989).
Use of a Microprocessor in the Control of Malignant Hypertension with Sodium Nitroprusside, Jackson RV, Love JB, Parkin WG, Wahlquist ML, Williams NS, Aust N Z J Med. Aug. 1977; 7(4):414-7.
Wilson R., "Integrated Circuits" of Computer Design, pp. 26-27, Jun. 1, 1989.
Written Opinion for International Application No. PCT/US2005/005829 dated Nov. 10, 2005.
Written Opinion for International Application No. PCT/US2007/017122 dated Feb. 19, 2008.
Written Opinion for International Application No. PCT/US2007/017123 dated Jan. 25, 2008.
Written Opinion for International Application No. PCT/US2007/017133 dated May 8, 2008.
Written Opinion for International Application No. PCT/US2007/022051 dated Mar. 7, 2008.

(56) References Cited

OTHER PUBLICATIONS

Written Opinion for International Application No. PCT/US2009/042494 dated Jan. 5, 2010.
Zales, S et al., Microprocessors and Microsystems vol. 14, No. 8, pp. 543-549, Oct. 1990.
Office Action dated Jun. 1, 2018 for Japanese Application No. 2015-555273, 12 pages.
Office Action dated Sep. 13, 2018 for Japanese Application No. 2015555273, 8 pages.
Notice of Acceptance dated Jul. 9, 2018 for Australian Application No. 2014209383, 3 pages.
Examination Report dated Dec. 4, 2018 for EP Application No. 14743307.2, 6 pages.
Office Action dated Nov. 7, 2018 for Chinese Application No. 201480006387.X, 15, pages.
Decision of Dismissal of Amendment dated Mar. 15, 2019 for Japanese Application No. 2015-555273, 6 pages.
Decision of Refusal dated Mar. 15, 2019 for Japanese Application No. 2015-555273, 2 pages.
Office Action dated Nov. 12, 2019 for U.S. Appl. No. 14/811,035, 22 pages.
Notice of Acceptance dated Mar. 30, 2020 for Australian Application No. 2018236693, 3 pages.
Office Action dated Dec. 9, 2019 for Canadian Application No. 2,896,100, 4 pages.

\* cited by examiner

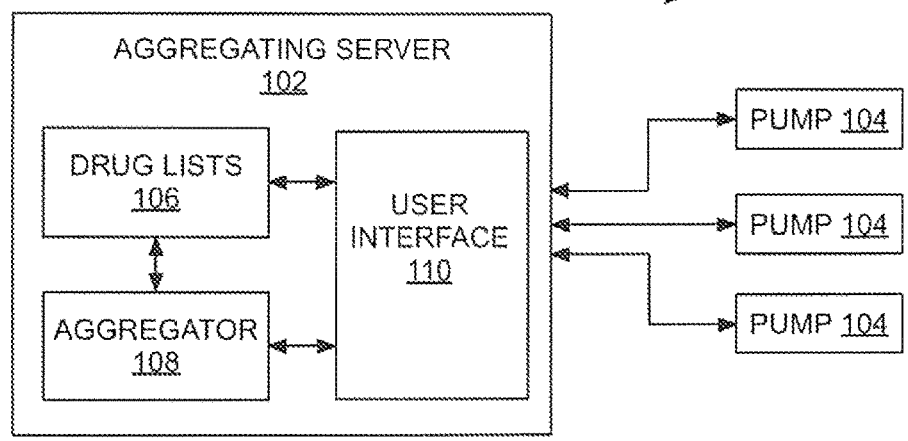
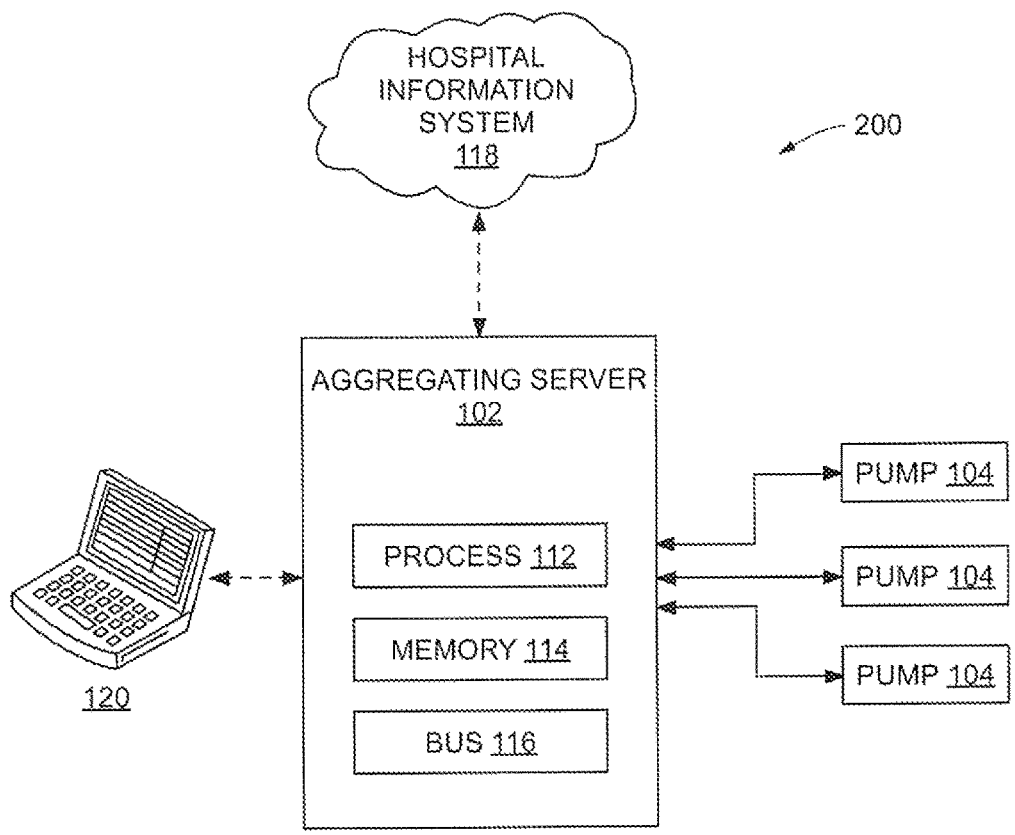

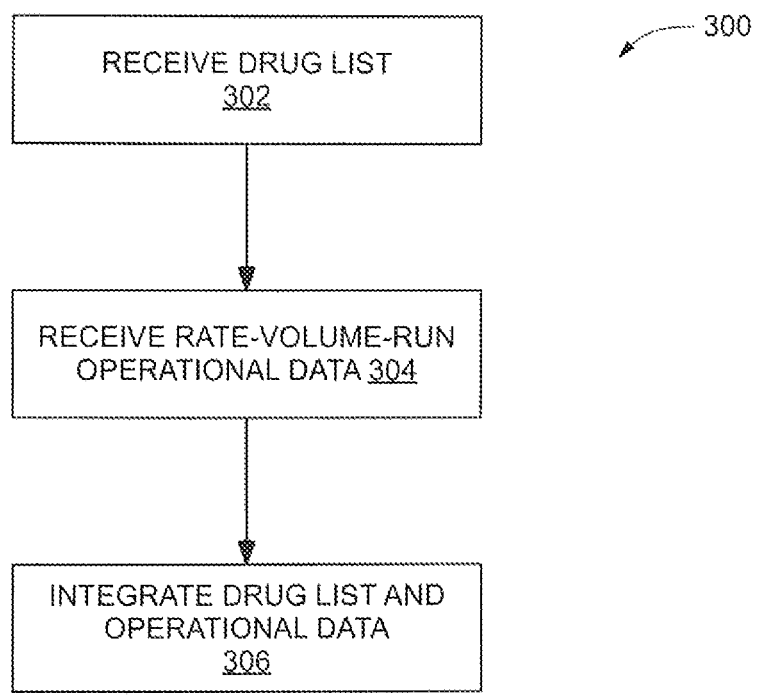

Fig. 4

| DISPLAYED NAME | CCA NAME | MED. AMT | MED. UNIT | DILUENT AMOUNT | DILUENT UNIT | MED. MAX. RATE | DOSE RATE DOSING UNIT | DOSE RATE LHL | DOSE RATE LSL | DOSE RATE USL | DOSE RATE UHL |
|---|---|---|---|---|---|---|---|---|---|---|---|
| EPINEPHRINE | ICU | 5 | mg | 250 | mL | | mcg/min | | 0.5 | 15 | |
| EPINEPHRINE | ICU | 16 | mg | 250 | mL | | mcg/min | | 0.5 | 15 | |
| EPINEPHRINE- mcg/kg/min DOSING | ICU | 5 | mg | 250 | mL | | mcg/kg/min | | 0.01 | 0.5 | |
| EPINEPHRINE- mcg/kg/min DOSING | ICU | 16 | mg | 250 | mL | | mcg/kg/min | | 0.01 | 0.5 | |
| ESMOLOL | ICU | 2000 | mg | 100 | mL | | mcg/kg/min | | 0.5 | 300 | 500 |
| HEPARIN | ICU | 25000 | units | 250 | mL | | units/hr | 50 | 200 | 2000 | 2500 |
| ISOPROTERENOL | ICU | 1 | mg | 50 | mL | | mcg/min | | 0.09 | 20 | |
| ISOPROTERENOL mcg/kg/min DOSING | ICU | 1 | mg | 50 | mL | | mcg/kg/min | | 0.01 | 0.3 | |

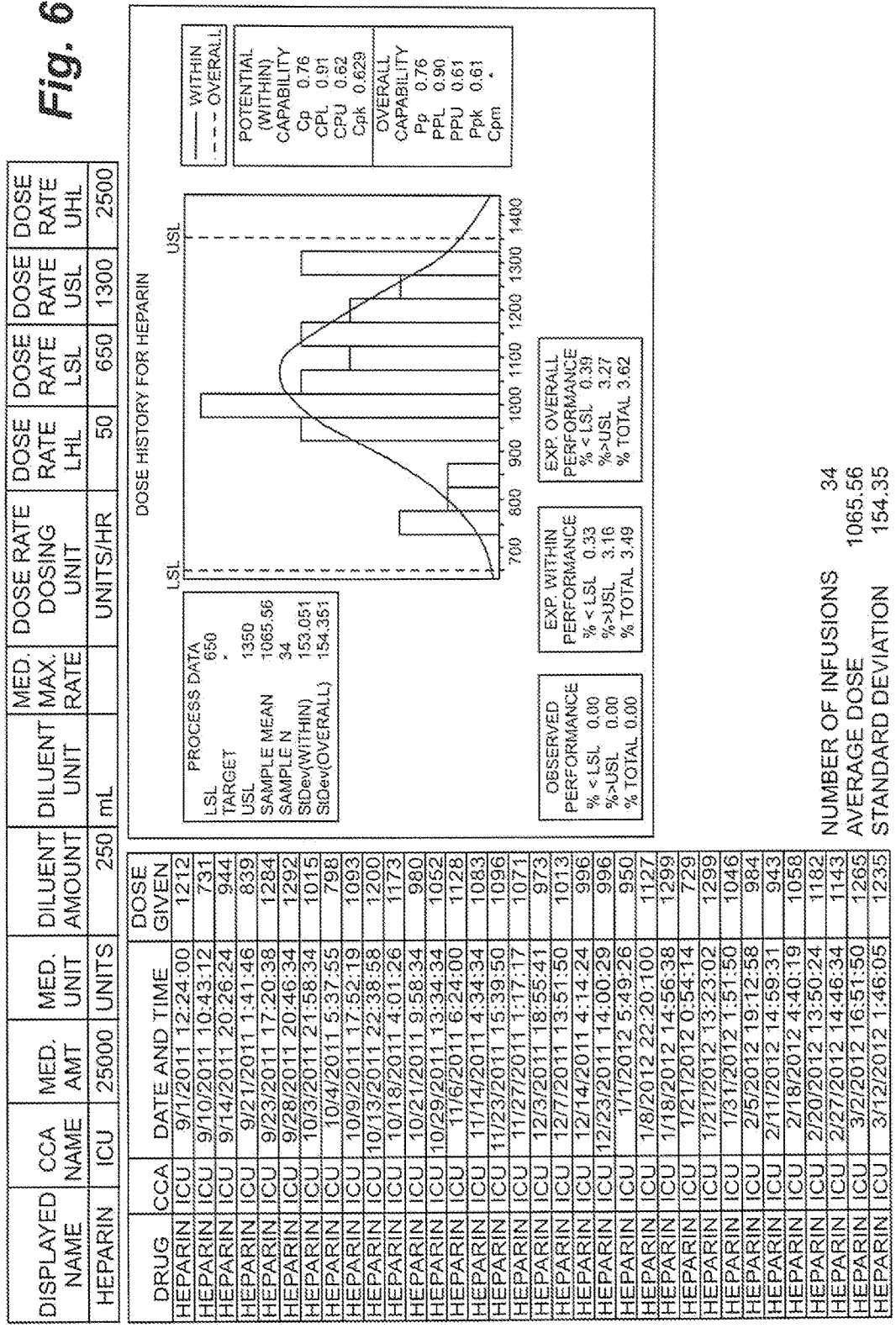

Fig. 7

| DISPLAYED NAME | CCA NAME | MED. AMT | MED. UNIT | DILUENT AMOUNT | DILUENT UNIT | MED. MAX. RATE | DOSE RATE DOSING UNIT | DOSE RATE LHL | DOSE RATE LSL | DOSE RATE USL | DOSE RATE UHL | COMPLI-ANCE |
|---|---|---|---|---|---|---|---|---|---|---|---|---|
| EPINEPHRINE | ICU | 5 | mg | 250 | mL | | mcg/min | | 0.5 | 15 | | 98.2% |
| EPINEPHRINE | ICU | 16 | mg | 250 | mL | | mcg/min | | 0.5 | 15 | | 99.5% |
| EPINEPHRINE-mcg/kg/min DOSING | ICU | 5 | mg | 250 | mL | | mcg/kg/min | | 0.01 | 0.5 | | 100.0% |
| EPINEPHRINE-mcg/kg/min DOSING | ICU | 16 | mg | 250 | mL | | mcg/kg/min | | 0.01 | 0.5 | | 100.0% |
| ESMOLOL | ICU | 2000 | mg | 100 | mL | | mcg/kg/min | | 300 | | | 100.0% |
| HEPARIN | ICU | 25000 | units | 250 | mL | | units/hr | 50 | 200 | 2000 | 2500 | 65.0% |
| ISOPROTERENOL | ICU | 1 | mg | 50 | mL | | mcg/min | | 0.09 | 20 | | 99.0% |
| ISOPROTERENOL-mcg/kg/min DOSING | ICU | 1 | mg | 50 | mL | | mcg/kg/min | | 0.01 | 0.3 | 500 | 98.5% |
| BASIC INFUSIONS | ICU | | | | | | NUMBER OF INFUSIONS | | 6 | | | 0.0% |

MEDICATION SAFETY DEVICES AND METHODS

RELATED APPLICATIONS

The present application is a National Phase entry of PCT Application No. PCT/US2014/012757, filed Jan. 23, 2014, which claims the benefit of U.S. Provisional Patent Application No. 61/757,587 entitled "MEDICATION SAFETY DEVICES AND METHODS" and filed Jan. 28, 2013, and U.S. Provisional Patent Application No. 61/826,253 entitled "MEDICATION SAFETY DEVICES AND METHODS" and filed May 22, 2013, each of which is incorporated herein by reference in its entirety.

TECHNICAL FIELD

This disclosure relates generally to medical systems, devices, and methods for facilitating the safe delivery of medication. In particular, it relates to systems, devices and methods for the operation of medical infusion pumps, and for the development and maintenance of drug libraries used in the operation of such pumps.

BACKGROUND

Medical infusion pumps are used to infuse liquids, such as nutrients and medicaments, into the circulatory system of a patient. Such pumps provide a wide range of flexibility in administering such fluids. For instance, the rate at which a medicament is introduced into the circulatory system can be variably programmed, the total volume to be administered can be pre-set, and the time for administering the medicament can be scheduled for automatic delivery at a certain periodicity. While the pre-programming of infusion rates, times and amounts with infusion pumps enables a wide variety of treatment protocols that would be impractical, expensive or unreliable if performed manually, it also presents the challenge of safely controlling the introduction of fluids into a patient when medical personnel are not continuously present.

Medical infusion pumps can be classified as large volume or small volume. Large volume pumps are typically used for medications and fluids, such as nutrients, that need to be delivered to patients in relatively large volumes compared to other medications and fluids, while small volume pumps can be used to infuse insulin or other medicines such as opiates. While small volume pumps can take different forms, syringe pumps are one of several types of pumps that can provide precision infusion of small amounts of fluid.

A syringe pump typically employs a pre-filled medication syringe that is mechanically driven under microprocessor control to deliver a prescribed amount or dose of a fluid at a controlled rate to a patient through an infusion line fluidly connected to the syringe. Syringe pumps typically include a motor that rotates a leadscrew. The leadscrew in turn activates a plunger driver which forwardly pushes a plunger within a barrel of the syringe. Pushing the plunger forward thus forces the dose of medication outwardly from the syringe, into the infusion line, and to the patient—typically, intravenously. Examples of syringe pumps are disclosed in U.S. Pat. No. 4,978,335 titled "Infusion Pump with Bar Code Input to Computer", U.S. Pat. No. 8,182,461 titled "Syringe Pump Rapid Occlusion Detection System", and U.S. Pat. No. 8,209,060 titled "Updating Syringe Profiles for a Syringe Pump," each of which is incorporated herein by reference in its entirety. As used throughout this disclosure, the term "syringe pump" is intended to generally pertain to any device which acts on a syringe to controllably force fluid outwardly therefrom.

Syringe pumps are used to control delivery to a patient of medications or fluids that include, but are not limited to: therapeutic agents; nutrients; drugs; medicaments such as antibiotics, blood clotting agents, and analgesics; and other fluids. The devices can be used to introduce the medications or fluids into the body of a patient utilizing any of several routes such as, for example, intravenously, subcutaneously, arterially, or epidurally.

To enhance patient safety during infusions, syringe pump manufacturers have developed so-called "smart" pumps that may provide functionality beyond just the delivery of fluids to a patient by the aforedescribed mechanical means. Smart pumps typically provide information concerning, or might even impose, safety limits on medication program parameters such as dose, concentration, and time, etc., for delivery of a particular medication from the pump to a particular patient. Consequently, more work may be required from practitioners to create and maintain so-called "drug libraries" associated with such safety limits. Provision of such functionality may be considered as being of higher importance in certain practices, protocols, and standardized procedures. There may be not as much emphasis or need for standardization, provision of pump safety limits, or restrictions on medication dosing rate ranges, however, with other practices and protocols. Thus, there is an unmet need for pumps that provide several levels of functionality.

In settings that typically do not require a high degree of functionality with safety limits and/or drug libraries for pumps, practitioners are usually accustomed to workflows that are much simpler than those of smart pumps. A simple workflow is usually defined as "Rate, Volume, Run" or a similar, basic controlled infusion protocol. Conversely, a more fully controlled infusion would typically employ applicable safety limits, which are commonly referred to as "hard" and "soft" limits, on delivery of a particular medication. A hard limit is often defined as a limit for which a selected infusion parameter that is outside of the limit results in generation of an alert and rendering of the pump inoperative or unable to accept selection or input of the parameter. Hard limits are typically set for high-risk drugs such as heparin. A soft limit, however, is often defined as a limit which may generate an alert but still may be overridden so that the infusion may proceed. When hard and/or soft limits are employed with a smart pump, information is usually input to the pump—or another system in communication with or controlling the pump—which includes data such as patient weight, the type of medication being infused, and the prescribed drug concentration. Typically a drug library contains a list of medications at predefined or standard concentrations, which in turn effectively determines safe dosing ranges. To program such a smart pump with a drug library, the practitioner would typically need to select the particular medication and concentration, enter the patient's weight, program the required infusion parameters such as dose and time, and then enter a command to start the infusion. These steps result in a more complicated workflow for practitioners.

Perhaps a larger challenge to smart pump workflows, however, is in preparing and setting running parameters, etc., before actual use of a pump with a patient. A clinical staff member such as a pharmacist would most likely need to develop a drug library with hard and soft limits for each medication and possibly for each drug concentration as well. In some cases these drug libraries or lists may exceed thousands of entries that need to be defined and entered prior to patient infusions. Developing and maintaining a drug library requires the management of a large number of drug lists, a large amount of hand-entered data, and therefore, involves a considerable amount of time. This problem is exacerbated in any transition to or from the traditional drug library storage component as part of a Hospital Information System (HIS).

It would therefore be useful and advantageous to provide medication safety devices and methods which would meet the needs of both a high and a lower functionality in setting limits and in drug libraries, and which could easily transition from a low functionality to create and maintain a more sophisticated drug library if desired.

SUMMARY

Embodiments of the disclosure provide novel and inventive medication safety devices and methods.

In an embodiment, a medication safety device can include a pump and a drug library in communication with the pump. The drug library can have upper hard and soft limits and lower hard and soft limits associated with at least one drug. A graphical user interface can display a bar chart showing upper and lower soft limit bars for the at least one drug. The upper and lower soft limit bars can be grabbed and dragged, in one particular embodiment, on the graphical user interface in touch-screen fashion to new positions associated with new upper and lower soft limits. The graphical user interface and associated hardware and software can be configurable to responsively re-analyze data and compare a particular infusion to the new upper and lower soft limits. Therefore, in a feature and advantage of various embodiments, user-interactive limiting values are implemented on a drug library for a syringe pump. For example, a slidable Lower Soft Limit (LSL), Upper Soft Limit (USL), Lower Hard Limit (LHL), and/or Upper Hard Limit (UHL) can be utilized to group and ungroup data in the drug library data sets to present limits in relation to known prior infusions. Clinicians or review boards can therefore readily examine the effect of the change to the limits on the number of acceptable and unacceptable infusions falling on some aspect of the LSL, USL, LHL, and/or UHL, or the capability index calculated. Embodiments therefore offer a holistic approach to the creation and maintenance of drug libraries.

In an embodiment, a method of creating a drug library comprises receiving a drug list, the drug list including a plurality of listed drug names, one or more delivery concentrations for each of the listed drugs, and one or more dose rates for each of the listed drugs, receiving operational data from at least one infusion pump, the operational data including information related to an infusion by the at least one infusion pump of at least one of the plurality of listed drugs, and integrating the drug list and the operational data.

In an embodiment, a medication safety system comprises at least one infusion pump, and an aggregating server operably coupled to the at least one infusion pump, the aggregating server comprising a processor and memory and configured to: receive a drug list, the drug list including a plurality of listed drug names, one or more delivery concentrations for each of the listed drugs, and one or more dose rates for each of the listed drugs, receive operational data from the at least one infusion pump, the operational data including information related to an infusion by the at least one infusion pump of at least one of the plurality of listed drugs, and integrate the drug list and the operational data to create a drug library.

In an embodiment, a method of transitioning an infusion pump comprises operating the infusion pump in a rate-volume-run mode, operating the infusion pump in a data-gathering mode, and operating the infusion pump in a smart-pump mode.

In an embodiment, an infusion pump comprises a pumping mechanism and a processor configured to operate the infusion pump in a rate-volume-run mode, operate the infusion pump in a data-gathering mode, and operate the infusion pump in a smart-pump mode.

In another feature and advantage of various embodiments, capability indices can be applied to drug library data sets to group and ungroup data in the data sets. For example, a change to the process capability index can automatically create a new chart for comparison having new boundaries or potential limits. Clinicians or review boards can therefore readily examine the affect of the change to the process capability index on the number of acceptable and unacceptable infusions falling on some aspect of the LSL, USL, LHL, and/or UHL.

In another feature and advantage of various embodiments, the user interface described herein can be presented on an operably coupled server, on an integrated viewing device, or on a particular pump. For example, an aggregating server can be operably coupled to one or more pumps, as will be described, for data-gathering utilizing one or more "data gathering" pumps. The aggregating server is configured to receive data from the one or more data gathering pumps and collect or aggregate said data for inclusion in drug library data sets. Thereafter, the user interface presenting drug library and limiting bars can be displayed on the aggregating server for limiting or other data set manipulation and analysis. In another example, the server can aggregate the data as described above, but particular limiting or other data set manipulation and analysis can be conducted on an integrated viewing device operably coupled to the aggregating server, such as a computer, tablet, smartphone, PDA, or other suitable device. In another example, the server can aggregate the data as described above, but particular limiting or other data set manipulation and analysis can be conducted on a pump or other medical device operably coupled to the aggregating server. In embodiments, the pump is the data gathering pump that transmitted infusion data to the aggregating server. In other embodiments, an individual pump can function as the aggregating server.

In another feature and advantage of various embodiments, dynamic data management is provided. In an embodiment, the data aggregated and/or presented can be filtered for patient populations, for example, pediatric patients, geriatric patients, high-risk patients, or low-risk patients, etc. Once aggregated, the data can be filtered according to input from the clinician, review board, or other user. For example, the appropriate limiting for pediatric patients can differ greatly from the limiting for adult patients. Therefore, it may be prudent to provide different upper and lower limits for these populations. Likewise, the limiting appropriate for high-risk adult patients can differ greatly from the limiting appropriate for low-risk adult patients. Data can also be filtered by type of drug, as the limiting appropriate for one drug may not be appropriate for another drug (or even for the same drug of a different concentration). Filters can therefore present the appropriate data sets so that informed decisions can be made to ensure the safety of patients being treated on pumps coupled to the system. Moreover, unlike the static reporting of traditional aggregators, wherein a text document is commonly presented via paper or electronically for board or clinician review, once new or changed limiting values are selected, the values can be automatically programmed to operably coupled pumps.

In another feature and advantage of various embodiments, an aggregating server is configured to calculate when a statistically significant number of data points has been obtained by one or more data gathering pumps. According to the understanding of one skilled in the art, a particular sample size is required in order to make inferences about a particular data population from a sample. Therefore, the aggregating server can automatically calculate the statistically significant number of data points required of any particular data population or data set, filtered or unfiltered. In other embodiments, the data manipulation described herein can also be performed on non-statistically significant sets of data.

In another feature and advantage of various embodiments, the aggregating server can be integrated with other statistically integrated tools and strategies for process improvement, such as Continuous Quality Improvement (CQI), Six Sigma, or Lean Processing, as well as any other suitable improvement process. In an embodiment, for example, any infusion outside of a LSL or USL can be logged as a CQI event. A review board, clinician, or other user can then review and adjust limiting based on the collected data and/or logged events to drive better practice. In other embodiments, the recorded CQI event is used to facilitate training of other clinicians or practitioners involved in the operation of the pumps.

The aforementioned aggregation and automated data analysis and manipulation therefore offers embodiments that reduce the amount of time required to establish drug profiles and limits around those profiles. For example, the manipulation of limits or capability indices in the aforementioned examples is much faster than hand-entering a drug, a drug concentration, the patient weight, and hand-calculating limit boundaries. Time and money is therefore saved by hospitals, clinicians, and administrators implementing embodiments of subject matter hereof.

In an embodiment, a method of establishing a smart pump through pump mode transition includes initial operation as a "Rate, Volume, Run" pump, intermediate operation as a data gathering pump, and final operation as a smart pump with drug library interaction. In embodiments, a transition plan aids practitioner training on, and implementation of, smart pumps and drug libraries. For example, a health care facility can have simple "Rate, Volume, Run" pumps, but desire to transition to smart pumps. According to embodiments, emulation of "Rate, Volume, Run" pumps by smart pumps enables practitioners in the facility to become accustomed to the physical designs, layouts, displays, user interfaces and input means, and ergonomics, etc., of the smart pumps before attempting to utilize or interact with advanced smart pump functionality.

In addition to emulation of "Rate, Volume, Run" pumps by smart pumps, data gathered can be analyzed to look for care area or practitioner irregularities or departures from best practices. That is, the smart pumps can employ or provide various data comparison schemes to identify beneficial or detrimental trends or practices in delivery of medication to patients. Also, based on a particular total data set within a hospital, an aggregating server can, for example, show practitioners how many different drug programs or profiles are needed to optimize specific patient population dosing ranges. As such, potentially detrimental "overlap" can be minimized or perhaps even eliminated. For example, one program or profile can be optimized for a neonatal intensive care unit and another program or profile can be optimized for an operating room or surgical suite, etc. Furthermore, "scenario analysis" can thus be optimized, allowing the software to recognize that a particular patient does not belong in a profile that may have been erroneously selected.

The above summary is not intended to describe each illustrated embodiment or every implementation of the subject matter hereof. The figures and the detailed description that follow more particularly exemplify these embodiments.

BRIEF DESCRIPTION OF THE DRAWINGS

Embodiments may be more completely understood in consideration of the following detailed description of various embodiments in connection with the accompanying figures, in which:

FIG. 1 is a block diagram of a system for the creation and maintenance of a drug library for the safe delivery of medication, according to an embodiment.

FIG. 2 is a block diagram of a system for the creation and maintenance of a drug library for the safe delivery of medication, according to an embodiment.

FIG. 3 is a flow diagram of a method of creating a drug library, according to an embodiment.

FIG. 4 is an illustration of an example of information that can be required when building a drug library, according to an embodiment.

FIG. 6 is an illustration of the example of FIG. 5, wherein new lower and upper soft limits have been set, according to an embodiment.

FIG. 7 is an illustration of the example of FIG. 4, additionally showing compliance for each drug in the library, according to an embodiment.

Figure 5:
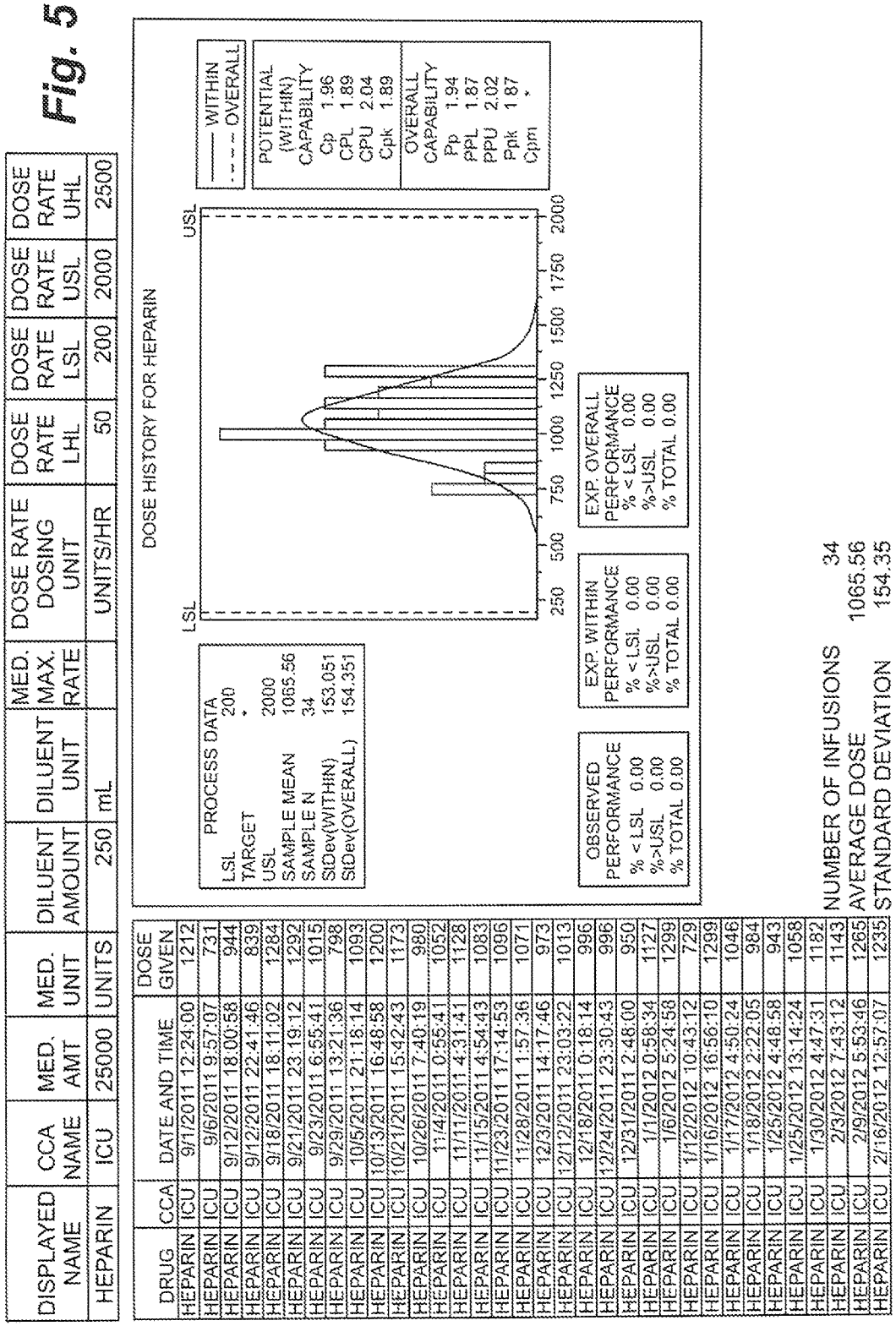
FIG. 5 is an illustration of an example of implementation of a method of building a drug library with upper hard and soft limits, and lower hard and soft limits, according to an embodiment.

While embodiments are amenable to various modifications and alternative forms, specifics thereof have been shown by way of example in the drawings and will be described in detail. It should be understood, however, that the intention is not to be limited to or by the particular embodiments described. On the contrary, the intention is to cover all modifications, equivalents, and alternatives falling within the spirit and scope of the subject matter hereof as defined by the appended claims.

DETAILED DESCRIPTION OF THE DRAWINGS

Devices and methods described in greater detail by way of examples herein provide for the scaling and building of drug libraries and medication safety software by way of graphical user interfaces. The devices and methods also provide valuable information on infusions performed in compliance with medication safety parameters, along with automatic or manual updating of drug libraries and a capability of selecting a particular drug in the library and viewing its delivery history and compliance data. The devices and methods further provide for the intuitive and relatively easy transitions from use of basic infusion pumps to smart pump functions. These features and functions are described by example in the following descriptions, with reference to the drawings.

Referring to FIG. 1, a system 100 for the creation and maintenance of a drug library for the safe delivery of medication generally comprises aggregating server 102 and one or more pumps 104 operably coupled to aggregating server 102. In an embodiment, aggregating server 102 comprises one or more drug lists 106, an aggregator 108, and a user interface 110.

According to an embodiment of aggregating server 102, a drug list 106 comprises a particular drug name, one or more delivery concentrations, and one or more dose rates for a particular drug. In embodiments, one or more drug lists 106 can comprise a separate list for each unique drug, or a concatenated list for all drugs.

Aggregator 108, in an embodiment, comprises an interface for one or more pumps 104 and storage for data received from the one or more pumps 104. In embodiments, aggregator 108 is configured to receive infusion data from pumps 104. Infusion data can comprise any data related to the infusion(s) performed by the transmitting pump. Referring to FIG. 4, examples of infusion data include the drug name, the pump location, the medication amount, the medication units, the diluent amount, the diluent units, the medication maximum rate, the dose rate dosing unit, dose timing, and limiting data. Infusion data can further comprise other general data about the patient with respect to the infusion, such as patient weight, patient age, patient gender, or other patient characteristics, such as patient risk characteristics. Aggregator 108 is further configured to store the infusion data, either in raw form or a synthesized form, for example, in the coupled storage of aggregating server 102, as will be discussed in reference to FIG. 2.

Generally, as will be discussed in further detail below, one or more pumps 104 send infusion data to aggregating server 102. In particular, aggregator 108 acts as a receiver for the transmitted infusion data. Aggregator 108 then interfaces with drug list 106 to combine or otherwise synthesize the particular drug list with the transmitted infusion data, where applicable. For example, the drug list 106 for HEParin will be integrated by aggregator 108 with transmitted infusion data related to HEParin. This data can then be interfaced to user interface 110 for further manipulation or analysis by a user of aggregating server 102. In general, as will be referred to herein, the combination of a drug list 106 and data from one or more pumps 104 creates a "drug library."

User interface 110 generally comprises a graphical user interface or other appropriate electronic display for viewing, analyzing, and modifying the synthesized drug library. For example, user interface 110 can be viewable on a computer monitor operably coupled to aggregating server 102. In embodiments, user interface 110 can be integrated into a tablet, smartphone, PDA, or other suitable device. Examples of user interactions with user interface 110 are discussed herein.

Pumps 104 each comprise, for example, a syringe pump to controllably force fluid outwardly therefrom to a patient. Further, an embodiment of pump 104 can comprise a processor and memory, while another embodiment of pump 104 can be in communication with another device which provides such processor and memory functions for interaction of pump 104 with aggregating server 102. In embodiments, pumps are used to control delivery to a patient of medications or fluids that include, but are not limited to: therapeutic agents; nutrients; drugs; medicaments such as antibiotics, blood clotting agents, and analgesics; and other fluids. The devices can be used to introduce the medications or fluids into the body of a patient utilizing any of several routes such as, for example, intravenously, subcutaneously, arterially, or epidurally. Each of pumps 104 comprises a communication interface to aggregating server 102. The communication interface can comprise any number of suitable protocols, and can be wired or wireless, in embodiments. Each of pumps 104 can interface directly to aggregator 108, other components of aggregating server 102.

Referring to FIG. 2, the one or more drug lists 106, aggregator 108, and user interface 110 can be implemented via aggregating server 102 as shown with processor 112, memory 114, and bus 116 in system 200.

Processor 112 can be any programmable device that accepts digital data as input, is configured to process the input according to instructions or algorithms, and provides results as outputs. In an embodiment, processor 112 can be a central processing unit (CPU) configured to carry out the instructions of a computer program. Processor 112 is therefore configured to perform basic arithmetical, logical, and input/output operations.

Memory 114 can comprise volatile or non-volatile memory as required by the coupled processor 112 to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the subject matter hereof.

Bus 116 comprises one or more subsystems for data transfer between processor 112 and memory 114. As such, bus 116, in an embodiment, is operably coupled to processor 112 and memory 114.

Moreover, referring again to FIG. 2, system 200 is further illustrated with Hospital Information System (HIS) 118 and interfacing device 120.

HIS 118 comprises the information or management system of a hospital, with all of its subcomponents and subsystems. HIS 118 can be configured to transmit data to aggregating server 102 for integration, by aggregator 108, into the drug libraries. Likewise, data can be transmitted from aggregating server 102 to HIS 118 for informational, reporting, or patient care purposes. Such data can be any kind of infusion or patient data as described above.

As shown in FIG. 2, interfacing device 120 is a laptop computer, but can also include a tablet, smartphone, PDA, or other suitable device as discussed above with respect to the integration of user interface 110.

As shown, HIS 118 and interfacing device 120 are operably coupled to aggregating server 102. Such coupling can be implemented by any suitable network protocol, including cellular-type networks such as GSM network protocols, UMTS network protocols, CDMA network protocols and the like or other wireless network protocols such IEEE 802.11 or Wi-Fi, IEEE 802.16 or WiMAX and the like. In embodiments, the coupling is via wired networks, such as Ethernet standards IEEE 802.3. In embodiments, interfacing device 120 can be utilized to build and manage a drug library by access of and interface with the aggregation and synthesizing of aggregator 108 and drug lists 106, in combination with input from HIS 118, where applicable.

Although not illustrated, in another embodiment, HIS 118 can comprise a plurality of HIS platforms or "data warehouses" that contain patient treatment information, etc. Additionally, various treatment and dosing schemes can be advantageously employed through gathering, selecting, and characterizing such patient data as described in, for example, U.S. Pat. No. 6,132,416 and U.S. Patent Application Pub. Nos. 2006/0000480, 2006/0137696, 2010/0057488, and 2011/0264462, each of which is incorporated herein by reference in its entirety.

In embodiments, referring to FIG. 3, a method of building a drug library 300 is illustrated. At 302, a drug list is received; for example, drug list 106. In embodiments, drug list 106 can be provided by, for example, HIS 118 or interfacing device 120, or user interface 110. In embodiments, drug list 106 can be hand-entered or batch downloaded. At 304, aggregating server 102 receives infusion and/or operational data from one or more pumps 104. In embodiments, aggregator 108 receives the infusion and/or operational data. The data can be stored in memory 114 by operation of processor 112 and bus 116. At 306, aggregator 108, in combination with drug lists 106, as described, aggregates and synthesizes the drug lists and received infusion data from pumps 104. As such, a drug library is created. The drug library can then be stored in memory 114 by operation of processor 112 and bus 116, or can be dynamically created by future synthesis of aggregator 108. The drug library can then be implemented on any pumps 104 or other medical devices utilizing similar data. In embodiments, the data gathering of pumps 104 and the implementation of the drug library are on the same pumps. In other embodiments, the data gathering of pumps 104 and the implementation of the drug library are on different pumps.

FIG. 4 illustrates an example of some information that can be used in building a drug library, including LHLs, LSLs, USLs, UHLs. Building a drug library often requires substantial research and data entry time prior to implementation of a pump utilizing such safety information. In contrast, a simple drug list, as mentioned above; for example, drug list 106 can contain relatively less information such as drug names, concentrations, and dose rates, according to an embodiment. For example, a drug list, when combined with a pump that is configured to be a "data gathering" pump, allows clinical personnel to build drug libraries based on current practices.

FIG. 5 illustrates an example of implementation of a method of building a drug library with upper hard and soft limits, and lower hard and soft limits, by way of a graphical user interface or other applicable electronic display and input device (collectively, as referenced throughout this document, "GUI"), such as user interface 110. In a right side inset in FIG. 5, an example of a GUI screen-shot bar chart titled "Dose History for HEParin" is shown. Referring to dashed vertical lines in leftmost and rightmost portions of this bar chart, it is visually apparent that the charted infusions are within the set LSL and USL. In an event that a practitioner would desire to further restrict administration of this drug, the LSL and USL bars could, for example, be "grabbed" and "dragged" on the GUI in touch-screen fashion to such new positions on the GUI as shown in FIG. 6, according to an embodiment. Examples of touch screen devices generally are disclosed in U.S. Patent Application Pub. Nos. 2006/0097991 titled "Multipoint Touchscreen" and in 2011/0193788 titled "Graphical Objects that Respond to Touch or Motion Input," which are incorporated herein by reference in their entireties. Examples of novel and inventive infusion pump technologies employing touch screen devices are disclosed in U.S. Pat. No. 5,485,408 titled "Pump Simulation Apparatus" and in U.S. Patent Application Pub. No. 2009/0270810 titled "Security Features for a Medical Infusion Pump," which are incorporated herein by reference in their entireties. In other embodiments, other graphical user interface or non-graphical user interface implementations for updating upper hard and soft limits and lower hard and soft limits are considered, such as through the use of slider bars, text boxes, radio buttons, keyed entry, or any other suitable interface embodiments.

The GUI and its associated hardware and software, for example, referring to FIGS. 1-2 and aggregating server 102 and pumps 104, in embodiments, can then be configured and provided to responsively re-analyze the data, and display on the chart how the infusions charted in FIG. 5 would have compared to the new LSL and USL as charted in FIG. 6. In this example, the new LSL would result in 99.67% compliance and the new USL would result in 96.84% compliance, with a total of 3.49% of all HEParin infusions falling outside the soft limits based on these settings. Upon completion of the analysis the new soft limits can be automatically or manually input to the drug library and uploaded to associated infusion pumps via, for example, a wired or wireless connection as operably coupled as discussed above. It is to be particularly appreciated and understood that adjusting infusion limits in such a manner results in a relatively fast and intuitive representation of the infusion data. This in turn allows a drug library administrator to quickly and easily analyze and change limits based on current best or desired practices.

Additionally, a compliance target can be assigned as a default, in an embodiment. For example, when building the drug library, the default value for compliance could be set to 98%. Based on this default value, the LSL and USL is suggested by the software.

Further, with reference to FIG. 7, compliance of the drug library can be intuitively displayed as shown in the rightmost column of the chart, with compliance being listed for each drug in the drug library. In embodiments, the compliance value or compliance percentage can be highlighted in red, green, or any other color or highlighting scheme to indicate the relative conformity to the particular USL and LSL. For example, a compliance value of 98.2% can be colored green, while a compliance value of 85.0% can be colored red, in order to better highlight to the user the compliance of each particular drug in the drug library. As such, for example, a summary of drug settings would be provided along with compliance data for particular infusions as compared to the settings. For further details, a user could "click on," "touch on," or otherwise select a particular drug in the library, with delivery history and compliance data for that particular drug (such as shown, for example, in FIG. 6) then being responsively communicated to and displayed on the GUI.

Referring to FIG. 7, information on basic or simple "Rate, Volume, Run" infusions as aforementioned can also be contained within the drug library (for example, in the bottom row of FIG. 7). In embodiments, the bottom row can be highlighted with coloring or other markings to indicate "Rate, Volume, Run" infusions from infusions utilizing limits and/or compliance with a drug library. The goal of a health care facility using such a medication safety device and method may be 100% compliance (i.e., zero basic infusions) for ensuring patient safety. By having both compliance and non-compliance (i.e., basic) infusion data presented together, practitioners and drug library administrators can effectively and easily monitor overall compliance with infusion safety limits.

Figure 8:
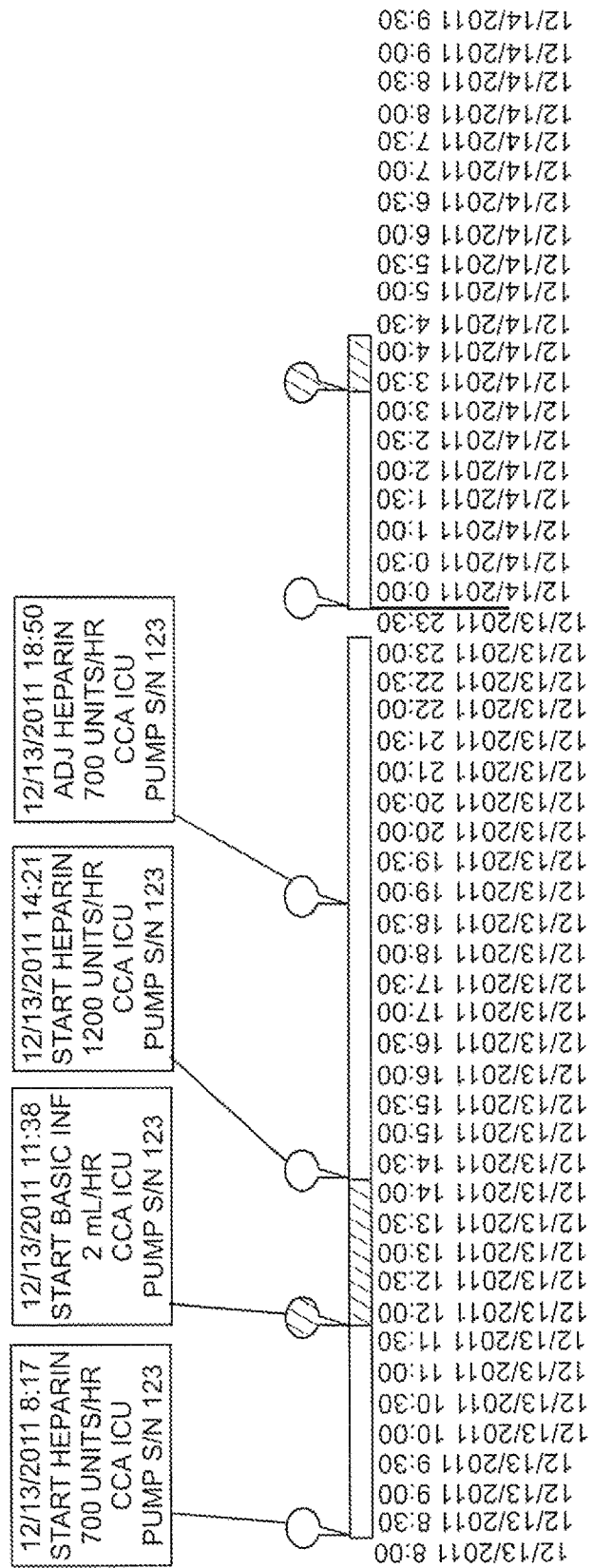
FIG. 8 is an illustration of an example of a timeline of infusions for a particular patient for evaluation of compliance with the drug library, according to an embodiment.

Referring now to FIG. 8, an example of a GUI timeline of infusions for a particular patient, for evaluation of compliance with the drug library is illustrated. In some cases, such as in emergency or time-critical situations, practitioners must deliver medications outside normal or otherwise acceptable parameters—such as when, for example, a patient is in imminent danger without administration of a particular life-saving medication. In such situations, practitioners typically will resort to administration of basic "Rate, Volume, Run" infusions or even rapid, manual injections of bolus doses. As shown in the example of FIG. 8, the GUI can display such events as a "pump history" log, thereby increasing awareness of potential occurrences of non-compliance with drug library safety limits. In embodiments, "Rate, Volume, Run" infusions can be highlighted in red, green, or any other color or highlighting scheme to easily allow the user to differentiate those infusions from infusions utilizing limits and/or compliance with a drug library. In this example, pump events are plotted on a timeline: a HEParin infusion was started at 8:17 on 12/13/2011; at 11:38 the same pump was started in a basic infusion mode; at 14:21 it was changed back to a HEParin infusion; and at 18:50 the rate was adjusted to 700 units/hr.

Regardless of a particular embodiment of subject matter hereof, it is to be particularly appreciated and understood that medication safety devices and methods—which have been described by example or otherwise contemplated herein—provide data visualization tools that are easy to use and that facilitate scaling and building of medication safety software and drug libraries, etc. It is also to be particularly appreciated and understood that such information can be efficiently and easily derived from current clinical practice data as aforedescribed.

In an embodiment, medication safety devices and methods can be configured to provide an intuitive transition from "Rate, Volume, Run" pumps to smart pumps. The configuration of the pump, whether a simple "Rate, Volume, Run" pump, data gathering pump, or smart pump, could be controlled by a health care facility to enhance patient protection while making administration of drug libraries and safety limits easier and more efficient.

Figure 9:
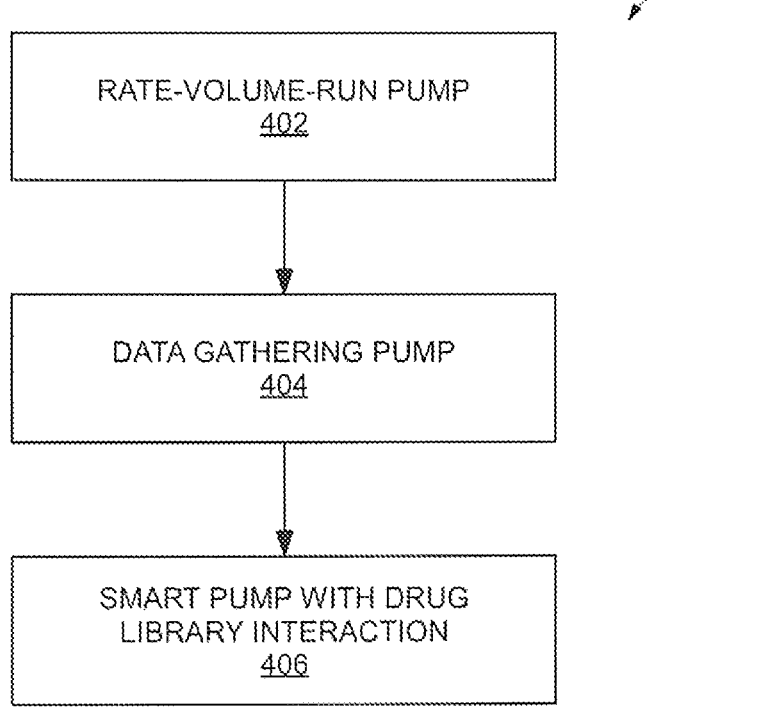
FIG. 9 is a flow diagram of a method of pump transition, according to an embodiment.

For example, referring to FIG. 9, a method of pump transition 400 comprises initial operation as a "Rate, Volume, Run" pump 402, an intermediate operation as a data gathering pump 404, and final operation as a smart pump 406 with drug library interaction.

In some instances, a transition plan can be of assistance for practitioner training on, and implementation of, smart pumps and drug libraries. For example, a health care facility can have simple "Rate, Volume, Run" pumps, but desire to transition to smart pumps. Referring to operation as a "Rate, Volume, Run" pump 402, embodiments can provide emulation of "Rate, Volume, Run" pumps by smart pumps. Such a feature allows practitioners in the facility to become accustomed to the physical designs, layouts, displays, user interfaces and input means, and ergonomics, etc., of the smart pumps before attempting to utilize or interact with advanced smart pump functionality. After a desired introductory period has elapsed, the health care facility's infusion pump administrator or manager could then, for example, adjust the pumps' operating parameters to require determination and selection of drugs, drug concentrations from drug lists, and patient weights in transition to smarter pump operations—to allow the practitioners to more easily become accustomed to entering and use of such infusion parameters.

For example, such emulation can be in combination with that of a data gathering pump as in data gathering pump 404 operation, wherein data being gathered is used to build the drug library automatically. In data gathering pump 404 operation, according to an embodiment, intermediate steps within data gathering operation are considered. For example, the data gathering pump 404 can first be implemented with a drug list. Subsequently, the data gathering pump 404 can transmit infusion data related to drugs on the drug list to aggregating server 102 for aggregation by aggregator 108.

As a last step in the transition process from "Rate, Volume, Run" pumps to smart pumps 406, upper and lower hard and soft limits could be employed and compliance could be logged and displayed as aforedescribed. In an embodiment, the smart pump 406 with drug library interaction can include utilizing a pump with a drug library downloaded to the pump, for example, on pumps 104, or by interfacing to the drug library stored on memory 114 of aggregating server 102.

It is to be appreciated and understood that, however, a particular facility could choose to implement any desired transition scheme such as, for example, immediately moving from "Rate, Volume, Run" pumps to smart pumps without the intermediate emulation of data gathering pumps; or emulations could be done in any order with any selected individual or groups of functions. Moreover, the particular mode can be selected among any of the operation as a "Rate, Volume, Run" pump 302, intermediate operation as a data gathering pump 304, or final operation as a smart pump 306 with drug library interaction.

Irrespective of a particular embodiment, it is to be appreciated and understood that medication safety devices and methods—as disclosed by example or otherwise contemplated herein—can be characterized in that intuitive visualization is employed for adjusting parameters of a drug library such as soft limits. Furthermore, the devices and methods can be characterized in that a transition from use of a basic infusion pump to a smart pump can be made by practitioners without a large amount of work for the creation of a drug library or without uncertainty or a lack of efficiency that often accompanies implementation of new devices and methods.

Figure 10:
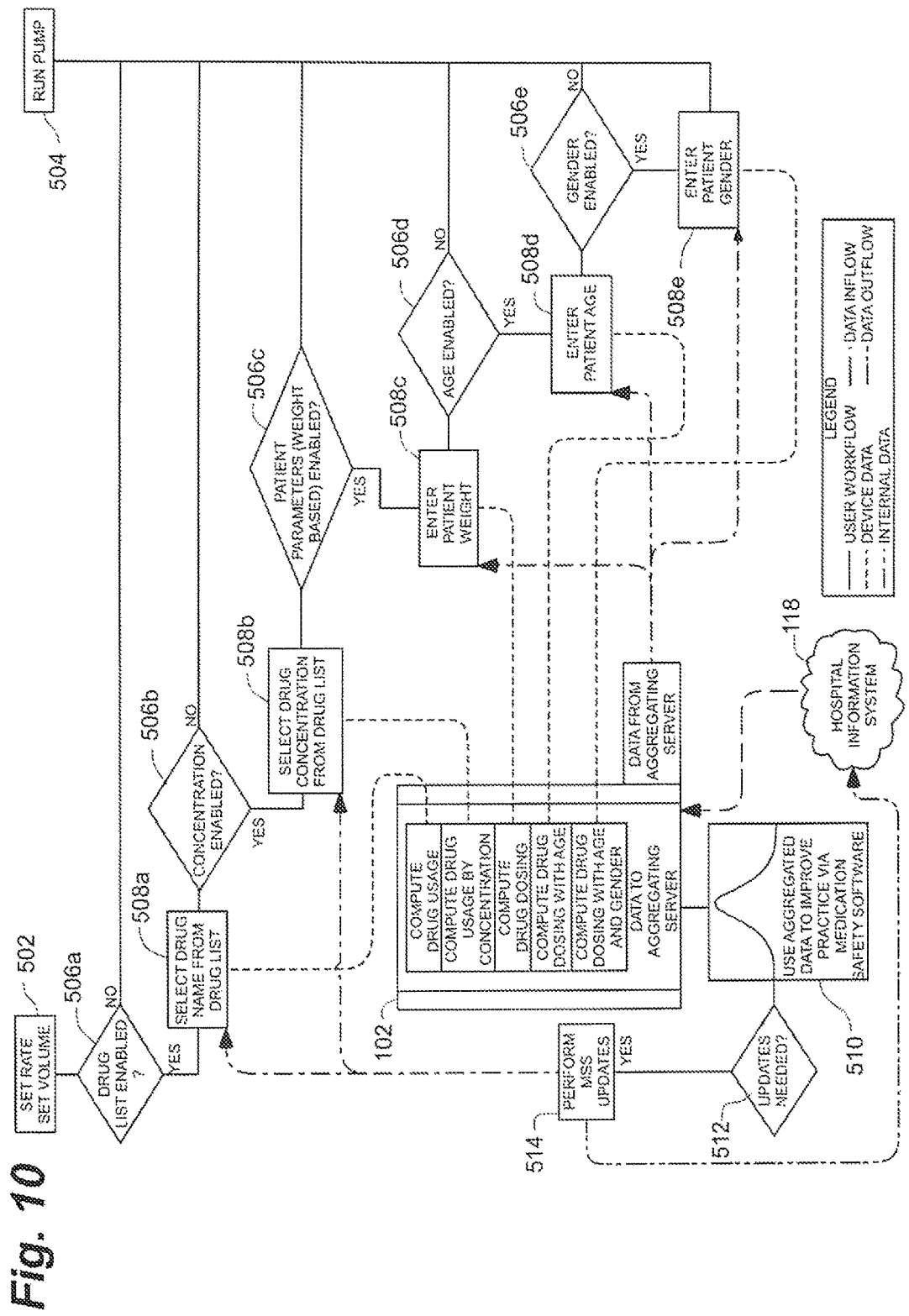
FIG. 10 is a flow diagram of a system for the creation and maintenance of a drug library, according to an embodiment.

Referring to FIG. 10, a flow diagram of a system for the creation and maintenance of a drug library, according to an embodiment of the subject matter hereof is illustrated. For diagram context, in most basic Rate-Volume-Run operation, for example, that of Rate-Volume-Run pump 402 in FIG. 9, a method is provided by steps 502 and 504, where the rate and volume are set at 502, and the pump is run at 504. In this example of embodiments of a Rate-Volume-Run pump 402, at 506a, a check is conducted to determine whether a drug list is enabled, in combination with user workflow, as depicted. In the Rate-Volume-Run operation, a drug list is not enabled, and operation therefore proceeds to the pump being run at 504.

In embodiments of a data gathering pump, for example, that of data gathering pump 404, data can be gathered for aggregation by aggregating server 102 by interaction with aspects of the pump. At 506a, if a drug list is enabled, a drug name is selected from the drug list at 508a. Subsequently, that data is transmitted by the pump device to aggregating server 102.

At 506b, a check is conducted to determine whether a concentration is enabled. If a concentration is not enabled, the operation again proceeds to the pump being run at 504. However, if a concentration is enabled, a drug concentration is selected from the drug list at 508*b*. Subsequently, that data is transmitted by the pump device to aggregating server 102.

At 506*c*, a check is conducted to determine whether patient parameters are enabled; for example, a weight-based infusion. If operation with patient parameters is not enabled, the operation again proceeds to the pump being run at 504. However, if operation with patient parameters is enabled, a patient weight is entered at 508*c*. Subsequently, that data is transmitted by the pump device to aggregating server 102.

At 506*d*, a check is conducted to determine whether age-based patient parameters are enabled. If operation with a patient's age is not enabled, the operation again proceeds to the pump being run at 504. However, if operation with a patient's age is enabled, a patient age is entered at 508*d*. Subsequently, that data is transmitted by the pump device to aggregating server 102.

At 506*e*, a check is conducted to determine whether gender-based patient parameters are enabled. If operation with a patient's gender is not enabled, the operation again proceeds to the pump being run at 504. However, if operation with a patient's gender is enabled, a patient age is entered at 508*e*. Subsequently, that data is transmitted by the pump device to aggregating server 102. Data can be transmitted serially to aggregating server 102 immediately after the aforementioned decision points, or in a batch after processing has completed and the pump is running. Therefore, embodiments of data gathering pump 404 can comprise any single or combination of the aforementioned checks and data transmissions, as well as any other suitable data gathering.

Referring, in an embodiment, to smart pump 406 operation, aggregating server 102 is configured to compute drug usage, drug usage by concentration, drug dosing, drug dosing with age, and/or drug dosing with age and gender, or any other appropriate drug or patient data synthesis. In an embodiment, the raw or aggregated data can be flowed back to the pumps from aggregating server 102, as illustrated by the internal data line.

In an embodiment, referring to 510, the aggregated data can be displayed and analyzed by aggregating server 102 in combination with user interface 110, as discussed in FIGS. 4-7, to improve the delivery of medication. As described, embodiments include the updating of limits and content of the drug library. At 512, a check can be conducted by aggregating server 102 or by flags on, for example, pumps 104, to determine if updated drug libraries are desired. In an embodiment, drug library updates can then be transmitted to the pumps at 514.

As described above, HIS 118 can be integrated into the data analysis of aggregating server 102, for example, as illustrated in FIG. 10. For example, when transmitting updates at 514 to the pumps 104, HIS 118 can likewise be updated. Similarly, HIS 118 can transmit data to aggregating server 102 for the inclusion of that data in the drug library analysis.

Regardless of particular components or modes of action, it is to be appreciated and understood that medication safety devices and methods—such as have been described by example or otherwise contemplated herein—can advantageously enhance accuracy, and thus safety and efficacy, in drug delivery to patients.

While medication safety devices and methods have been particularly shown and described with reference to the accompanying figures and specification, it should be understood however that other modifications thereto are of course possible; and all of them are intended to be within the true spirit and scope of novel and inventive devices and methods described herein. Thus, configurations and designs of various features can be modified or altered depending upon particular embodiments. For example, sequencing of various method steps described by example or otherwise contemplated herein can be re-ordered as may be desired in a particular embodiment.

Although subject matter hereof has been described in a context of "syringe pumps", it is to be appreciated and understood that the subject matter may also be applicable to virtually any infusion delivery device such as, for example, so-called "large volume" pumps and "ambulatory" pumps among others.

It is also to be understood that dimensioning and scaling of the drawings herein have been chosen to clearly show details of example embodiments. Thus, in some embodiments it is possible that spacing between, or orientations of, various features might be variable and visually different from those illustrated. In any event, dimensioning and scaling can vary significantly across various embodiments of medication safety devices and methods.

It is also to be understood in general that any suitable alternatives may be employed to provide novel and inventive medication safety devices and methods as described by example or otherwise contemplated herein.

Accordingly, these and other various changes or modifications in form and detail may also be made, without departing from the true spirit and scope of medication safety devices and methods that may be defined by the appended claims.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the subject matter hereof may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

What is claimed is:

1. A medication safety system, comprising:
   one or more data gathering infusion pumps adapted to controllably force fluid outwardly therefrom to a patient; and
   an aggregating server configured to receive operational data from the one or more data gathering infusion pumps, the aggregating server including—
     a drug list including a plurality of listed drug names;
     an aggregator adapted to integrate the drug list and the received operational data to create a drug library having upper hard and soft limits and lower hard and soft limits associated with at least one drug; and
     a graphical user interface for viewing, analyzing and modifying the drug library, the graphical user interface displaying a bar chart showing the infusion data and upper and lower soft limit bars for the at least one drug, wherein the upper and lower soft limits can be manipulated by a practitioner to restrict administration of the at least one drug by grabbing and dragging the upper and lower soft limit bars on the graphical user interface in touch-screen fashion to new positions associated with new upper and lower soft limits;

wherein the aggregating server is configured to compare the received operational data with the updated upper and lower soft limits to determine a compliance value representative of a percentage of the received infusion data that falls within the updated upper and lower soft limits; and wherein upon completion, the drug library is uploaded to an infusion pump for implementation.

2. The medication safety system of claim 1, wherein the graphical user interface and associated hardware and software is configurable to responsively re-analyze data and compare a particular infusion to the new upper and lower soft limits.

3. The medication safety system of claim 2, wherein the drug library is updated with the new upper and lower soft limits after the re-analyzing.

4. The medication safety system of claim 3, wherein the drug library is configured to be automatically updated with the new upper and lower soft limits after the re-analyzing.

5. The medication safety system of claim 3, wherein the drug library is configured to be manually updated with the new upper and lower soft limits after the re-analyzing.

6. The medication safety system of claim 3, wherein the updated drug library is configured to be uploaded to the syringe pump after the updating.

7. The medication safety system of claim 6, wherein the updated drug library is wirelessly uploaded to the syringe pump after the updating.

8. The medication safety system of claim 2, wherein the syringe pump is adapted to transmit infusion data to the aggregator, and to receive infusion data for the at least one drug including the updated upper and lower soft limits from the aggregator.

9. The medication safety system of claim 1, wherein the medication safety system is configured to suggest the upper and lower soft limits.

10. The medication safety system of claim 9, wherein the medication safety system is configured to suggest the upper and lower soft limits based on a compliance target default value.

11. The medication safety system of claim 10, wherein the graphical user interface is configured to display compliance data.

12. The medication safety system of claim 11, wherein the compliance data includes an indication of conformity with the compliance target default value.

13. The medication safety system of claim 12, wherein the indication is a color or highlighting scheme.

14. The medication safety system of claim 10, wherein the medication safety system is configured to log compliance data as a continuous quality improvement (CQI) event.

15. The medication safety system of claim 1, wherein the graphical user interface is configured to display a delivery history for the at least one drug.

16. The medication safety system of claim 1, wherein the graphical user interface is configured to display a timeline of infusions for a particular patient for evaluation of compliance with the drug library.

17. The medication safety system of claim 1, wherein the graphical user interface is configured to display a pump history log.

18. The medication safety system of claim 17, wherein the graphical user interface is configured to display a color or highlighting scheme of the pump history log to differentiate events that are in compliance with the drug library from events that are non-compliant with the drug library.

19. The medication safety system of claim 1, wherein the medication safety system is configured to provide emulation of a "rate, volume, run" pump operating scheme by the syringe pump.

20. The medication safety system of claim 19, wherein the emulation facilitates transition from a "rate, volume, run" pump operating scheme to an operating scheme in which one or more safety limits for delivery of a particular medication to a particular patient are automatically imposed.

21. The medication safety system of claim 19, wherein the emulation facilitates transition from a "rate, volume, run" pump operating scheme, to an intermediate pump operating scheme, to an operating scheme in which one or more safety limits for delivery of a particular medication to a particular patient are automatically imposed.

22. The medication safety system of claim 1, wherein the infusion pump in which the drug library is uploaded for implementation is one of the one or more data gathering infusion pumps.

* * * * *